(12) United States Patent
Donegan et al.

(10) Patent No.: US 11,912,983 B2
(45) Date of Patent: Feb. 27, 2024

(54) POLYANIONIC ACIDS TO IMPROVE RECOVERY AND MINIMIZE SYSTEM LOSS

(71) Applicant: Waters Technologies Corporation, Milford, MA (US)

(72) Inventors: Michael Donegan, Charlton, MA (US); Martin Gilar, Franklin, MA (US); Matthew Lauber, North Smithfield, RI (US); Scott Mccall, Smithfield, RI (US); Pamela Iraneta, Brighton, MA (US); Kerri Smith, Marlborough, MA (US)

(73) Assignee: Waters Technologies Corporation, Milford, MA (US)

( * ) Notice: Subject to any disclaimer, the term of this patent is extended or adjusted under 35 U.S.C. 154(b) by 426 days.

(21) Appl. No.: 17/112,502

(22) Filed: Dec. 4, 2020

(65) Prior Publication Data

US 2021/0171932 A1     Jun. 10, 2021

Related U.S. Application Data

(60) Provisional application No. 62/944,145, filed on Dec. 5, 2019.

(51) Int. Cl.
*C12N 15/10*     (2006.01)
*C12N 15/113*    (2010.01)

(52) U.S. Cl.
CPC .......... *C12N 15/101* (2013.01); *C12N 15/113* (2013.01); *C12N 2310/11* (2013.01); *C12N 2310/315* (2013.01)

(58) Field of Classification Search
CPC ............ C12N 15/101; C12N 2310/315; C12N 15/113; C12N 2310/11; G01N 33/5306
See application file for complete search history.

(56) References Cited

U.S. PATENT DOCUMENTS

| | | | |
|---|---|---|---|
| 5,869,152 A | 2/1999 | Colon | |
| 6,686,035 B2 | 2/2004 | Jiang et al. | |
| 7,442,299 B2 | 10/2008 | Lee et al. | |
| 7,562,367 B1 | 7/2009 | Arad | |
| 8,658,038 B2 | 2/2014 | Rustamov et al. | |
| 9,380,520 B2 | 6/2016 | Lee et al. | |
| 2012/0055860 A1 | 3/2012 | Wyndham | |
| 2019/0091657 A1 | 3/2019 | Lawrence et al. | |
| 2021/0171932 A1 | 6/2021 | Donegan et al. | |
| 2022/0017887 A1* | 1/2022 | Donegan | ........... B01J 41/10 |

FOREIGN PATENT DOCUMENTS

| | | |
|---|---|---|
| EP | 3450972 A1 | 3/2019 |
| GB | 2445442 A | 7/2008 |
| WO | 199622299 A1 | 7/1996 |
| WO | 199729825 A1 | 8/1997 |
| WO | 199856797 A1 | 12/1998 |
| WO | 2003080834 A2 | 10/2003 |
| WO | 2006127973 A2 | 11/2006 |
| WO | 2007064809 A2 | 6/2007 |
| WO | 2010072821 A1 | 7/2010 |
| WO | 2011073235 A1 | 6/2011 |
| WO | 2017155848 A1 | 9/2017 |
| WO | 2017155870 A1 | 9/2017 |
| WO | 2017155884 A1 | 9/2017 |
| WO | 2017189357 A2 | 11/2017 |
| WO | 2019067637 A1 | 4/2019 |
| WO | 2020055922 A1 | 3/2020 |

OTHER PUBLICATIONS

Gilar et al. "Purification of crude DNA oligonucleotides by solid-phase extraction and reversed-phase high-performance liquid chromatography." J. Chromatogr. A. 890(2000): 167-177.

International Search Report and Written Opinion issued in International Application No. PCT/IB2020/061554 dated Mar. 24, 2021.

Szabo et al. "High Performance Anion Exchange and Hydrophilic Interaction Liquid Chromatography Approaches for Comprehensive Mass Spectrometry-Based Characterization of the N-Glycome of a Recombinant Human Erythropoietin." JCA. 17.4(2018): 1559-1574.

\* cited by examiner

*Primary Examiner* — Pancham Bakshi
(74) *Attorney, Agent, or Firm* — WOMBLE BOND DICKINSON (US) LLP; Deborah M. Vernon; Ricardo Joseph

(57) ABSTRACT

The present technology relates to a method of separating a sample comprising oligonucleotides. The method includes injecting a polyphosphonic acid at a concentration of between about 0.01 M to about 1 M into the sample comprising oligonucleotides. The method also includes flowing the sample and polyphosphonic acid through a liquid chromatography column and separating the oligonucleotides.

15 Claims, 15 Drawing Sheets
Specification includes a Sequence Listing.

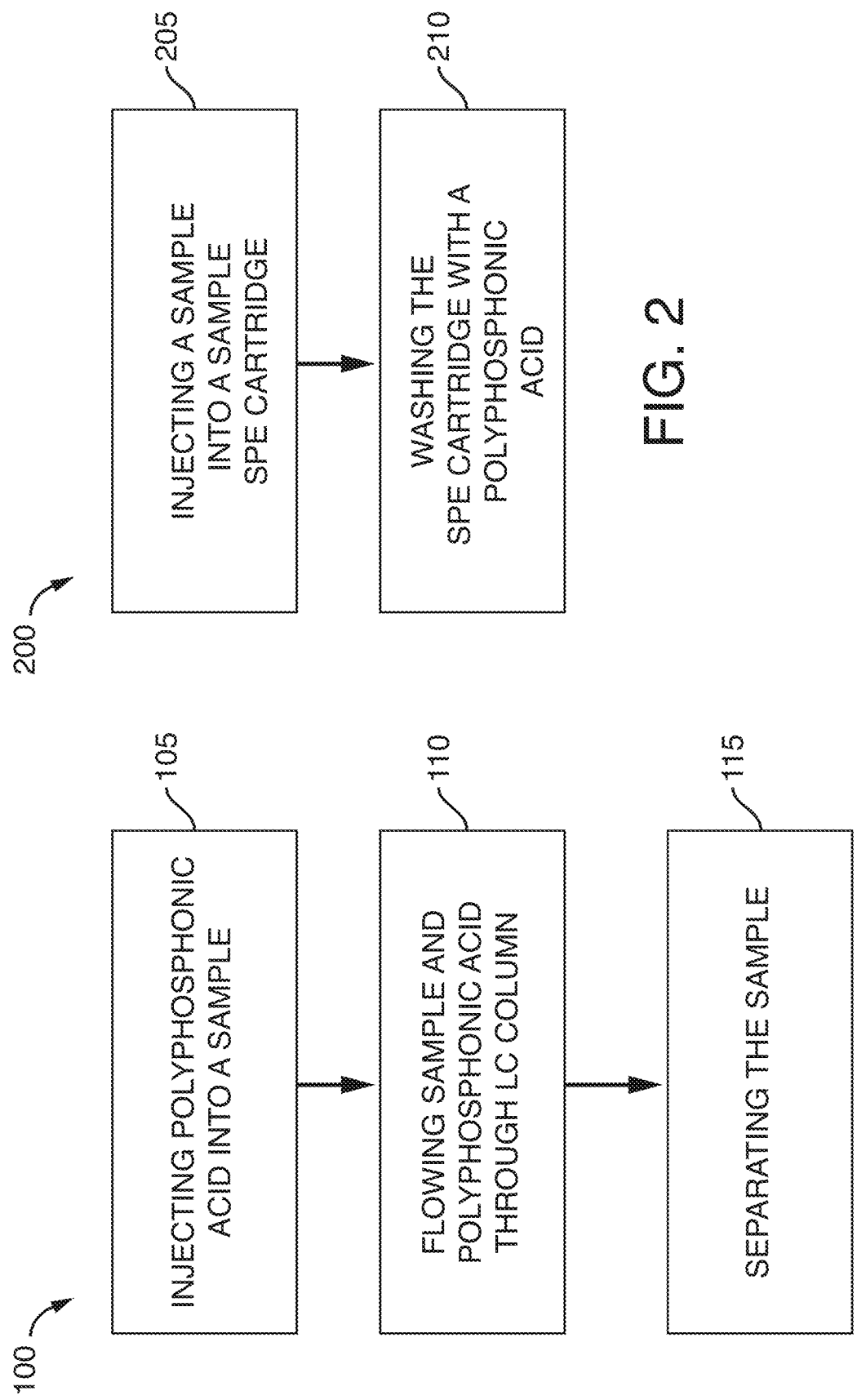

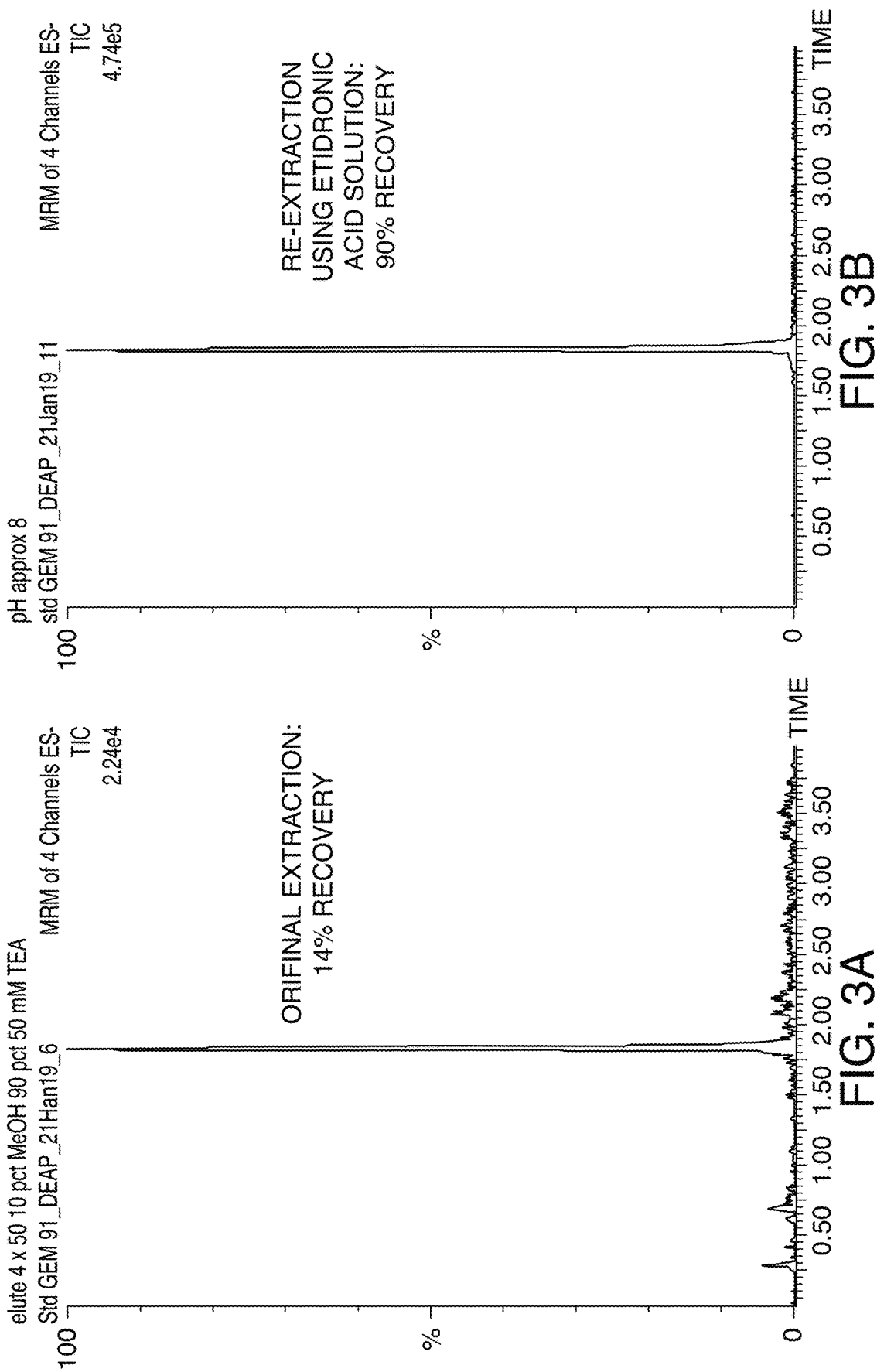

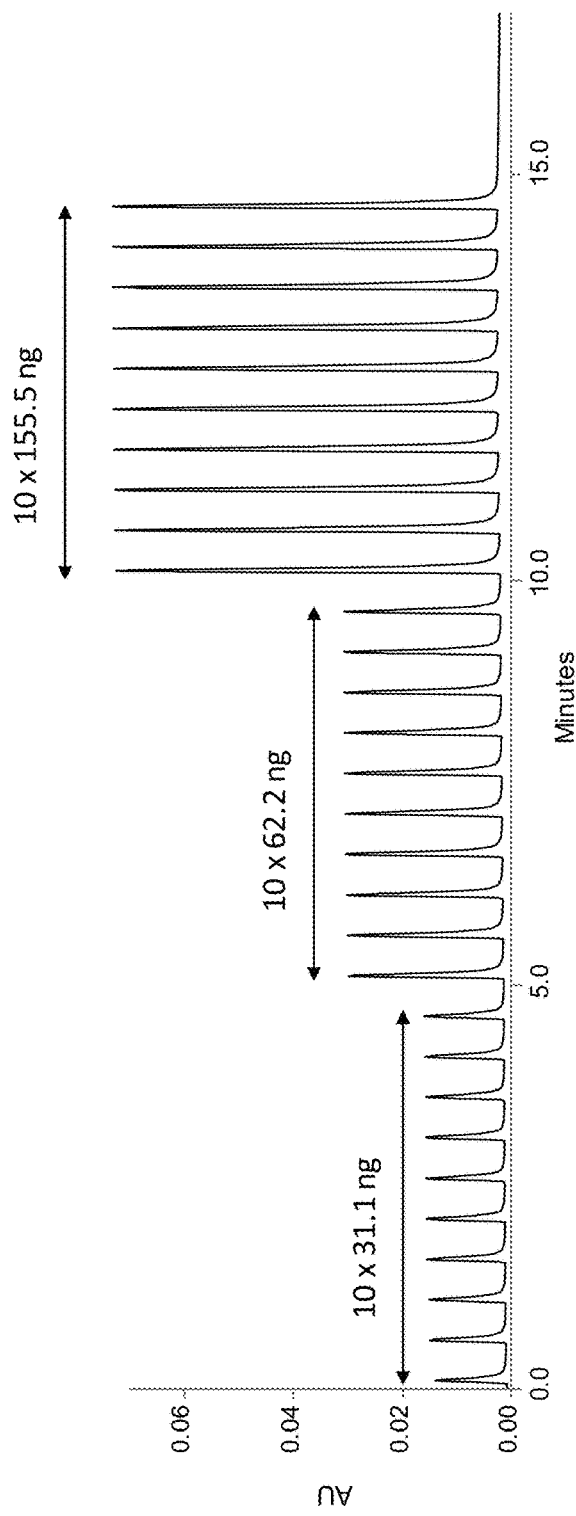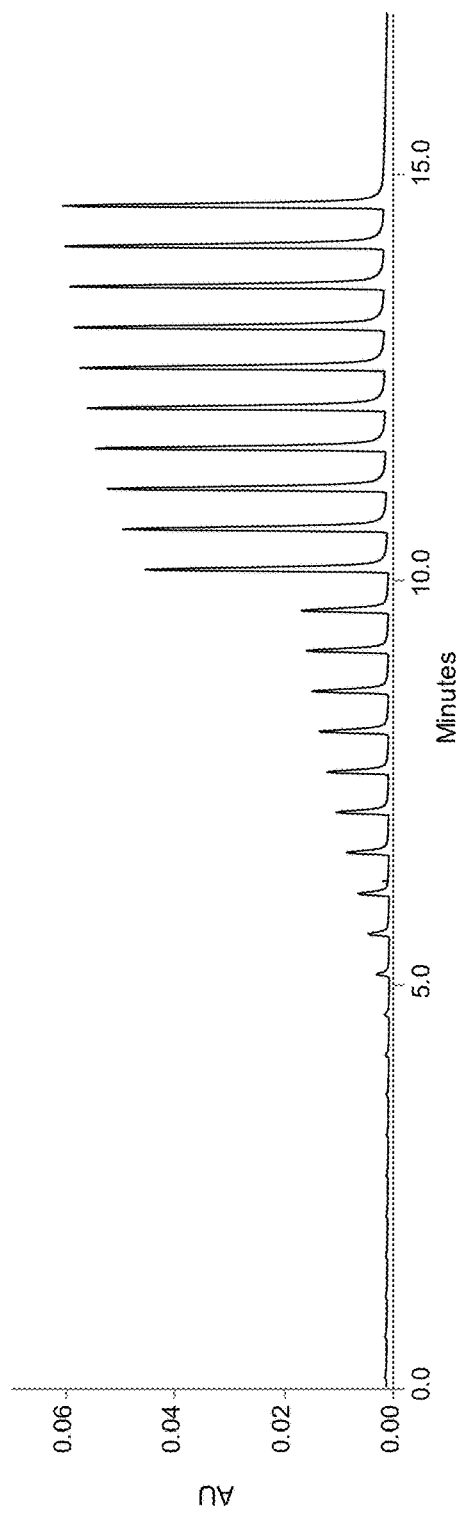
Fig. 9A
Fig. 9B

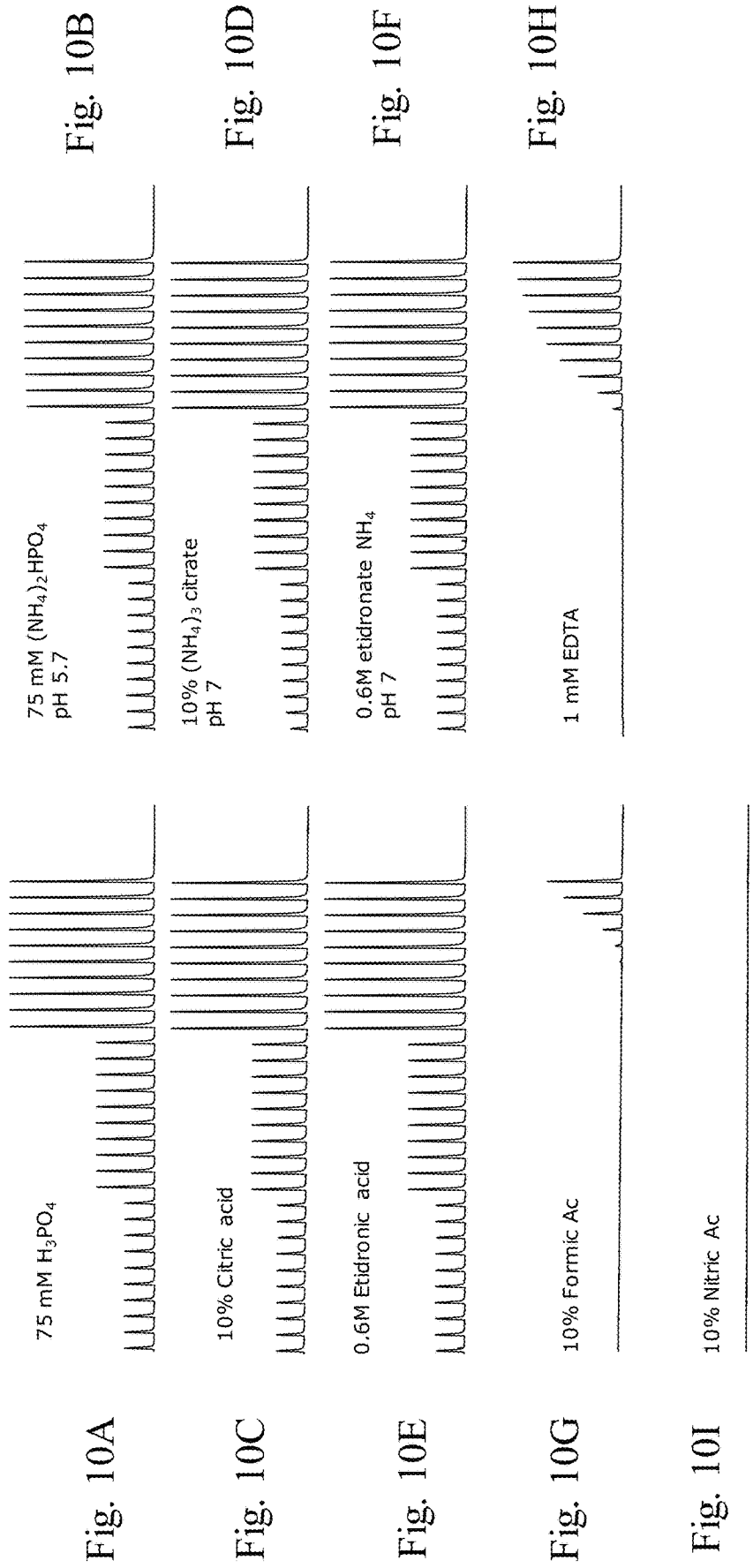

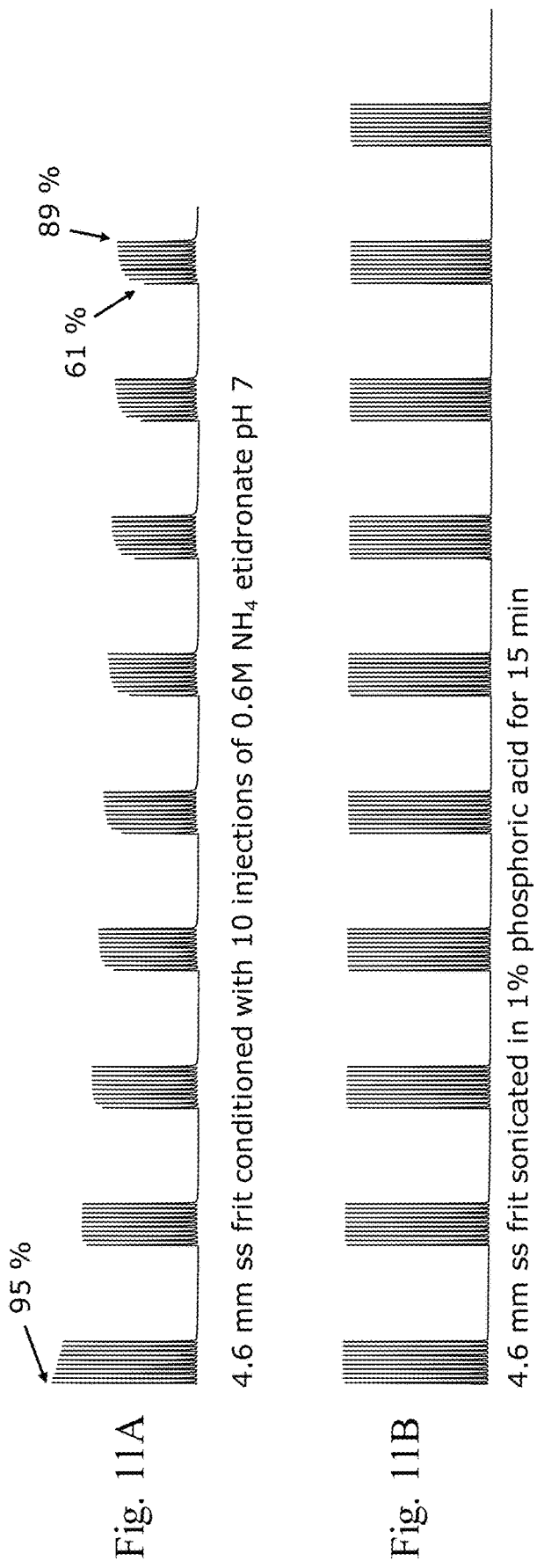

SEQUENCE LISTING

<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 1
ctctcgcacc catctctctc cttct    25

POLYANIONIC ACIDS TO IMPROVE RECOVERY AND MINIMIZE SYSTEM LOSS

CROSS-REFERENCE TO RELATED APPLICATIONS

This application claims the benefit of U.S. Provisional Application Ser. No. 62/944,145, filed on Dec. 5, 2019, the entire contents of which is incorporated by reference herein.

SEQUENCE LISTING

This application incorporates by reference the Sequence Listing contained in the ASCII text file with the file name W-4144-US02_Sequence Listing_ST25.txt, created Dec. 3, 2020 with the size of 467 bytes, being submitted concurrently herewith.

FIELD OF THE TECHNOLOGY

The present disclosure relates to the use of polyanionic acids to improve recovery and minimize system loss. More specifically, the present disclosure relates to the use of polyanionic acids to reduce nonspecific binding in chromatographic systems, sample vials, and in solid phase extraction devices to improve sample recovery and minimize loss of analytes to the system.

BACKGROUND

Oligonucleotides are polymeric sequences of nucleotides (RNA, DNA, and their analogs) that are utilized extensively as PCR (polymerase chain reaction) and microarray-based reagents in life science research and DNA-based diagnostic test kits (as primer and probe reagents). With increased frequency, they are being developed as therapeutic drugs for a wide range of disease conditions. Only a few FDA-approved oligonucleotide-based therapeutic drugs are on the market today, but there are over 100 currently in the clinical pipeline and many more in earlier stages of development.

Oligonucleotides developed as therapeutics can take a variety of forms, from antisense oligonucleotides (ASOs), small interfering RNAs (siRNA), small hairpin RNAs (shRNAs), and micro RNAs (miRNAs) that can effect "gene silencing," which is down-regulating or turning off the expression of specific genes/proteins; to Aptamers that behave like small molecule drugs and bind to specific disease targets; to messenger RNAs (mRNAs) that can be very long, and are being designed to up-regulate expression of a particular protein. To enhance their stability and/or cellular uptake in-vivo, oligonucleotide therapeutics often incorporate chemically-modified nucleotides, are PEGylated, or are otherwise conjugated to other chemical moieties. And like other biologics, the biophysical characteristics and purity of these molecules must be precisely understood and controlled to meet regulatory requirements.

Oligonucleotides are produced through an automated solid-phase synthesis process. Typical lengths range from 20 to 80 nucleotides (mRNAs being an exception, as they can be 1,500 or more nucleotides long). Depending on the application, synthesis scales can vary from nanograms to kilograms. While the synthesis process is efficient, it invariably results in truncated sequences and other process-related by-products/impurities that need to be separated and removed in order to meet purity requirements.

However, due to their polyanionic nature oligonucleotides are very sticky. They tend to adhere to metallic system components in the fluidic chromatographic path such as preheaters, frits, and column bodies. Oligonucleotides are also known to non-specifically bind to plasma proteins, sample plates, and vials. Weak anion exchange (WAX) solid phase extraction (SPE) is the method of choice for bioanalysis of oligonucleotides but variable recoveries have led to a lukewarm acceptance.

In addition, anionic glycans can also be difficult to analyze by liquid chromatography because of their propensity to adsorb to metal surfaces. Similar to oligonucleotides, this can result in poor recovery.

SUMMARY

The poor recovery of oligonucleotides using WAX and SPE may be due to both the chemistry of the SPE plate and the nonspecific binding of the analyte encountered during extraction. The poor recovery of glycans in liquid chromatography can also be the result of the chemistry of the stationary phase or the nonspecific binding of the analyte encountered during extraction. The present technology solves the problems of the prior art by addressing the non-specific binding issues that plague the analysis of analytes, particularly oligonucleotides, and especially when the analyte concentration is low. By addressing the non-specific binding issues of oligonucleotide analysis, analyte recovery can be increased.

Polyphosphonic acids such as etidronic acid, and nitrilotri (methylphosphonic acid) act as agents to competitively bind to surfaces that would normally attract polyanionic analytes such as oligonucleotides and glycans. This results in a reduction of the nonspecific binding of those analytes due to high molar excess of the polyphosphonic acid. Due to their charged nature even at higher pH, these additives will not be chromatographically retained and therefore not be a cause of ion suppression in LC/MS (liquid chromatography/mass spectrometry) analysis. The ability to reduce non-specific binding can be impactful for both SPE recovery and system based solutions.

The use of these polyanionic acids to mask or passivate non-specific binding from the system and can be utilized in several ways: (1) pre-analysis passivation by flushing the system prior to analysis by infusing polyanionic acids through the system; (2) dynamic passivation by injecting plugs of polyanionic acids (e.g., polyphosphonates) via an injector repetitively; (3) including polyanionic acids in the sample as masking agents (e.g., polyphosphonates are present in molar excess); and (4) elution solvents by introducing polyanionic acids into a SPE device to elute or release tightly bound analytes from the stationary phase.

While many of the aspects of the technology provided below relate to oligonucleotides and/or glycans, other biological samples can benefit from the methods, kits, and techniques presented herein. For example, the present technology is also applicable to the extraction of any phosphorylated compound, including the following applications: glyphosate (and related organophosphorus compounds), phospholipids, bisphosphonate drugs, peptides, and proteins.

In one aspect, the technology relates to a method of separating a sample comprising oligonucleotides. The method includes injecting a polyphosphonic acid at a concentration of between about 0.01 M to about 1 M into the sample comprising oligonucleotides. The method also includes flowing the sample and polyphosphonic acid through a liquid chromatography column and separating the oligonucleotides. The method can include one or more of the embodiments described herein.

In some embodiments, the concentration of polyphosphonic acid is between about 0.01 M to about 0.1 M. The concentration of polyphosphonic acid can be between about 20 mM to about 50 mM. The concentration of polyphosphonic acid can be between about 30 mM to about 40 mM.

In some embodiments, between about 1 pg to about 1 mg of the polyphosphonic acid is injected into the sample. The polyphosphonic acid can be etidronic acid. The polyphosphonic acid can be nitrilotri(methylphosphonic acid).

In some embodiments, walls of the liquid chromatography column are formed of metal.

The sample can include phosphorylated oligonucleotides. In some embodiments, the phosphorylated oligonucleotides comprise nucleotides and at least one nucleotide is adenosine triphosphate.

In some embodiments, the polyphosphonic acid is etidronic acid at pH of 8.5 and the oligonucleotide comprises nucleotides and at least one nucleotide is adenosine triphosphate.

The polyphosphonic acid can be a bisphosphonic acid. In some embodiments, the bisphosphonic acid is selected from the group consisting of clodronic acid, pamidronic acid, alendronic acid, neridronic acid, and olpadronic acid.

In another aspect, the technology relates to a method of performing solid phase extraction. The method includes injecting a sample comprising oligonucleotides into a solid phase extraction cartridge comprising a stationary phase. The oligonucleotides are retained by the stationary phase. The method also includes washing the solid phase extraction cartridge with a polyphosphonic acid at a concentration of between about 0.01 M to about 1 M to elute the oligonucleotides from the solid phase extraction cartridge. The method can include one or more of the embodiments described herein.

In some embodiments, the concentration of polyphosphonic acid is between about 0.01 M to about 0.1 M. The concentration of polyphosphonic acid can be between about 20 mM to about 50 mM. In some embodiments, the concentration of polyphosphonic acid is between about 30 mM to about 40 mM.

In some embodiments, about 1 pg to about 1 mg of the polyphosphonic acid is injected into the sample.

The polyphosphonic acid can be etidronic acid. In some embodiments, polyphosphonic acid is nitrilotri(methylphosphonic acid).

In some embodiments, walls of the solid phase extraction cartridge are formed of plastic.

In some embodiments, the sample comprises phosphorylated oligonucleotides. The phosphorylated oligonucleotides comprise nucleotides and at least one nucleotide is adenosine triphosphate. In some embodiments, the polyphosphonic acid is etidronic acid at pH of 8.5 and the oligonucleotide comprises nucleotides and at least one nucleotide is adenosine triphosphate.

In some embodiments, the polyphosphonic acid is a bisphosphonic acid. In some embodiments, the bisphosphonic acid is selected from the group consisting of clodronic acid, pamidronic acid, alendronic acid, neridronic acid, and olpadronic acid.

In some embodiments, the solid phase extraction cartridge is a packed syringe. The solid phase extraction cartridge can be a well plate.

In another aspect, the technology relates to a method of separating a sample comprising glycans. The method includes injecting a polyphosphonic acid at a concentration of between about 0.01 M to about 1 M into the sample comprising glycans. The method also includes flowing the sample and polyphosphonic acid through a liquid chromatography column and separating the glycans. The method can include one or more of the embodiments described herein.

In some embodiments, the concentration of polyphosphonic acid is between about 0.01 M to about 0.1 M. The concentration of polyphosphonic acid can be between about 20 mM to about 50 mM. In some embodiments, the concentration of polyphosphonic acid is between about 30 mM to about 40 mM.

In some embodiments, between about 1 pg to about 1 mg of the polyphosphonic acid is injected into the sample.

The polyphosphonic acid can be etidronic acid. In some embodiments, the polyphosphonic acid is nitrilotri(methylphosphonic acid). In some embodiments, the polyphosphonic acid is a bisphosphonic acid. The bisphosphonic acid can be selected from the group consisting of clodronic acid, pamidronic acid, alendronic acid, neridronic acid, and olpadronic acid.

In some embodiments, walls of the liquid chromatography column are formed of metal.

In another aspect, the technology features a method of performing solid phase extraction. The method includes injecting a sample comprising glycans into a solid phase extraction cartridge comprising a stationary phase. The glycans are retained by the stationary phase. The method also includes washing the solid phase extraction cartridge with a polyphosphonic acid at a concentration of between about 0.01 M to about 1 M to elute the glycans from the solid phase extraction cartridge. The method can include one or more of the embodiments described herein.

In some embodiments, the concentration of polyphosphonic acid is between about 0.01 M to about 0.1 M. The concentration of polyphosphonic acid can be between about 20 mM to about 50 mM. In some embodiments, the concentration of polyphosphonic acid is between about 30 mM to about 40 mM.

In some embodiments, between about 1 pg to about 1 mg of the polyphosphonic acid is injected into the sample.

In some embodiments, the polyphosphonic acid is etidronic acid. The polyphosphonic acid can be nitrilotri (methylphosphonic acid). In some embodiments, the polyphosphonic acid is a bisphosphonic acid. In some embodiments, the bisphosphonic acid is selected from the group consisting of clodronic acid, pamidronic acid, alendronic acid, neridronic acid, and olpadronic acid.

In some embodiments, walls of the solid phase extraction cartridge are formed of plastic. In some embodiments, the solid phase extraction cartridge is a packed syringe. The solid phase extraction cartridge can be a well plate.

In yet another aspect, this technology relates to the use in the reduction of non-specific binding encountered during sample preparation such as, for example, but not limited to oligonucleotides, glycans or any phosphorylated compound in a glass or polypropylene container (e.g., glassware, sample vials, etc.).

BRIEF DESCRIPTION OF THE DRAWINGS

The technology will be more fully understood from the following detailed description taken in conjunction with the accompanying drawings, in which:

FIG. 1 is a flow chart of a method of separating a sample, according to an illustrative embodiment of the technology.

FIG. 2 is a flow chart of a method of performing solid phase extraction, according to an illustrative embodiment of the technology.

FIG. 3A is a chromatogram showing the recovery of GEM 91 oligonucleotide from a WAX SPE plate using MeOH and TEA, according to an illustrative embodiment of the technology.

FIG. 3B is a chromatogram showing the recovery of GEM 91 oligonucleotide from a WAX SPE plate using etidronic acid, according to an illustrative embodiment of the technology.

FIG. 9A is a chromatogram showing absorbance over time of three different concentration levels of 25 mer phosphorothioate oligonucleotide, including a titanium frit deactivated with inert coating of hybrid organic-inorganic silica, according to an illustrative embodiment of the technology.

FIG. 9B is a chromatogram showing absorbance over time of three different concentration levels of 25 mer phosphorothioate oligonucleotide, including a stainless steel frit, according to an illustrative embodiment of the technology.

FIG. 10A, FIG. 10B, FIG. 10C, FIG. 10D, FIG. 10E, FIG. 10F, FIG. 10G, FIG. 10H, and FIG. 10I are chromatograms showing absorbance over time of three different concentration levels of 25-mer phosphorothioate oligonucleotide injected on a sonicated stainless steel frit with various acids, according to an illustrative embodiment of the technology.

FIG. 11A is a chromatogram showing injections of adenosine 5'-α,β-methylene) diphosphate (AMPcP) with experimental conditions including a stainless steel frit conditioned that was first conditioned with 5×10 µL injections of 0.6M $NH_4$ etidronate with pH 7, according to an illustrative embodiment of the technology.

FIG. 11B is a chromatogram showing injections of adenosine 5'-α,β-methylene) diphosphate (AMPcP) with experimental conditions including a stainless steel frit sonicated in 1% phosphoric acid for 15 minutes, according to an illustrative embodiment of the technology.

DETAILED DESCRIPTION

Figure 4A:
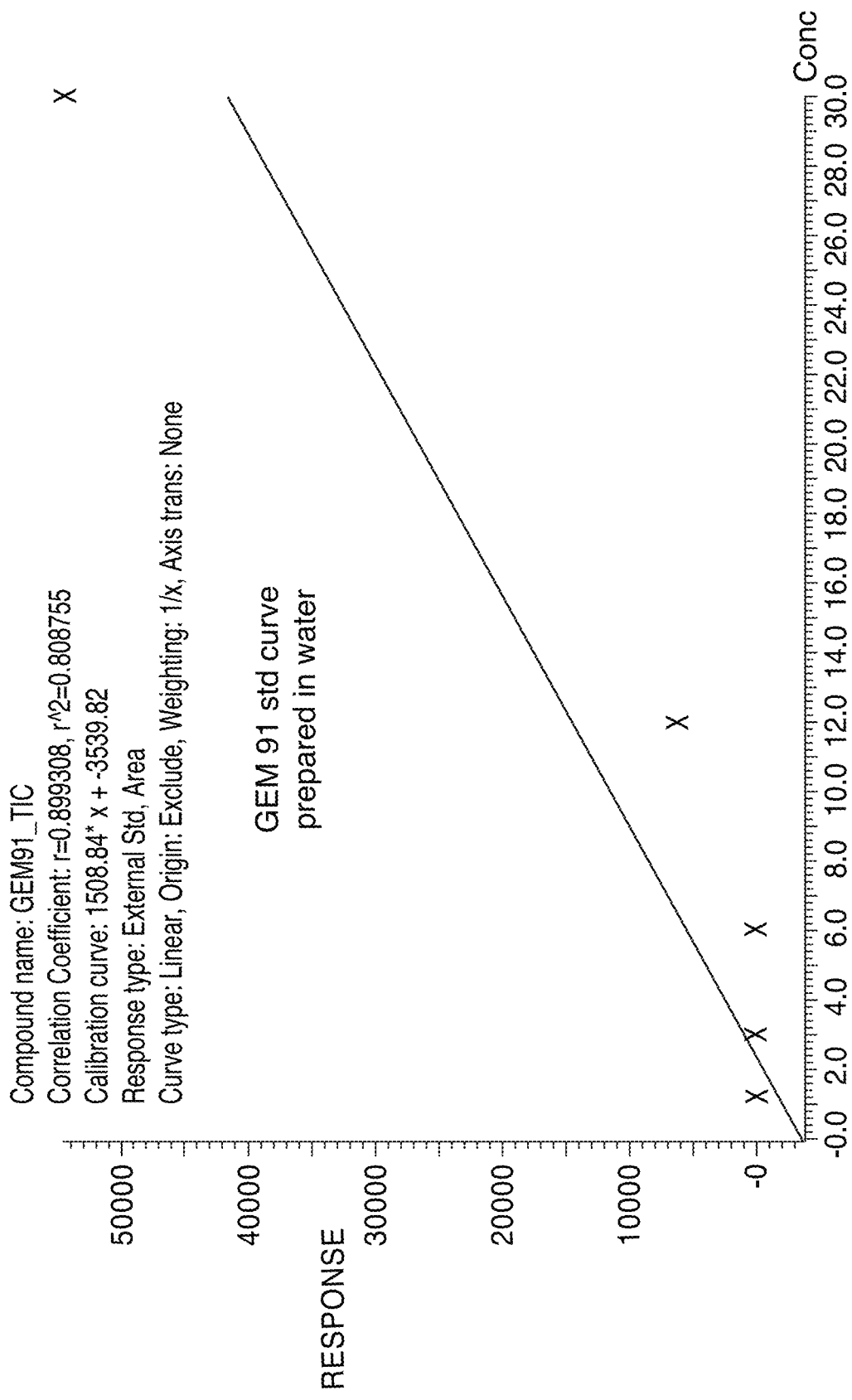
FIG. 4A is a linear calibration curve prepared for a 25-mer oligonucleotide GEM 91 prepared in water, according to an illustrative embodiment of the technology.

The present technology solves the problems of the prior art by addressing the non-specific binding issues that plague the analysis of analytes, particularly oligonucleotides, and especially when the analyte concentration is low, for example at concentrations in the few PPB or PPM range. By addressing the non-specific binding issues of oligonucleotide analysis, analyte recovery can be increased.

Referring to FIG. 1, the technology relates to a method 100 of separating a sample that includes an oligonucleotide or a glycan. The method includes injecting a polyphosphonic acid into the sample (105). The sample can include one or more oligonucleotides, one or more glycans, or a combination thereof.

When the sample includes oligonucleotides, different forms of oligonucleotides can be present in the sample. For example, the sample can include any combination of antisense oligonucleotides (ASOs), small interfering RNAs (siRNA), small hairpin RNAs (shRNAs), micro RNAs (miRNAs), or any other form of oligonucleotide.

The polyphosphonic acid can be injected into the sample (105) at a concentration that is a molar excess. A molar excess of polyphosphonic acid is a concentration that is, for example, double or triple the concentration of the oligonucleotides or analytes in the sample. The polyphosphonic acid can be injected into the sample (105) at a concentration that is a molar excess relative to the oligonucleotide. For example, if the oligonucleotide concentration is 20 mM, a molar excess of polyphosphonic acid may be 40 mM or greater. In certain embodiments, the concentration of polyphosphonic acid can be between about 0.01 M to about 1 M. In some embodiments, the concentration of polyphosphonic acid is between about 0.01 M to about 0.1 M. In some embodiments, the concentration of polyphosphonic acid is between about 20 mM to about 50 mM or between about 30 mM to about 50 mM.

Alternatively, the concentration of polyphosphonic acid can be expressed in grams. In some embodiments, between about 1 pg to about 1 mg of polyphosphonic acid can be injected into the sample.

The polyphosphonic acid is injected into the sample and not into the mobile phase. Generally, injecting additives (including polyphosphonic acids) into a mobile phase can result in ion suppression, i.e., an adverse effect on detector (e.g., mass spectrometer) response due to reduced ionization efficiency because the additives contend with the analyte for ionization. This results in the presence of species other than the analyte of interest being detected by the mass spectrometer. In contrast, injecting a polyphosphonic acid into a sample, instead of a mobile phase, removes the risk of ion suppression because the polyphosphonic acid elutes early (i.e., in the void volume) during chromatographic separation and thus can be excluded from mass spectrometric analysis (i.e., by sending the early eluting compounds/additives/polyphosphonic acid to waste).

Phosphonates and polyphosphonic acids of varying molecular properties can be used in this technology. The chemical structures described by Diab et al, *Bisphosphonates: Pharmacology and Use in the Treatment of Osteoporosis*, Osteoporosis (Fourth Edition), 2013, pages 1859-1872 and Bishop et al., *Bisphosphonates*, Osteogenesis Imperfecta, 2014, pages 495-500 can be used in this technology and are hereby incorporated herein by reference. Log D values should be given consideration along with the pKa of the phosphonic acid moieties. The pKa properties of the phosphonic acid moieties should be considered relative to the experimental conditions employed. In practice, it is desired to have one or more of the acidic groups of the phosphonic acid species ionized at the experimental pH, such that chromatographic retention of the phosphonate does not occur. In practice, the pH and concentration at which a phosphonate is employed should be considered to optimize its utility.

The polyphosphonic acid can be a bisphosphonic acid. In some embodiments, the bisphosphonic acid can have Formula I:

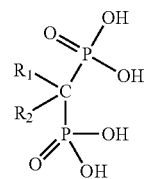

Formula I where $R_1$ and $R_2$ are each independently be selected from the group consisting of OH, H, $(C_1$-$C_{20})$alkyl, halogen, amine, and $(C_1$-$C_{20})$amine. In some embodiments, $R_1$ and $R_2$ can be optionally substituted.

Examples of bisphosphonic acids include etidronic acid, clodronic acid, pamidronic acid, alendronic acid, neridronic acid and olpadronic acid. The chemical structures of exemplary bisphosphonic acids are shown below.

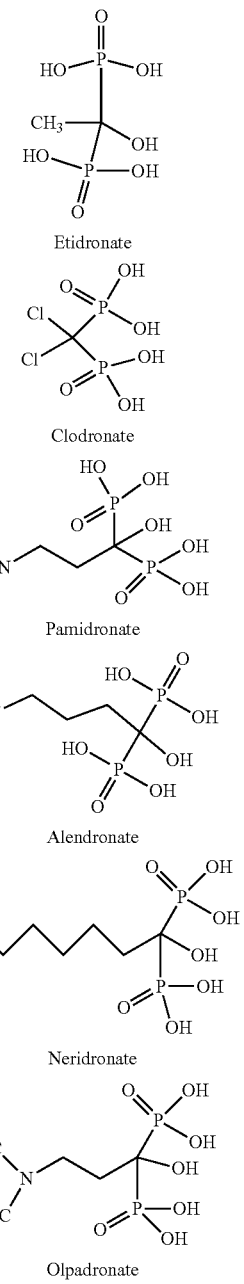

In some embodiments, $R_1$ and $R_2$ are each independently be selected from the group consisting of H, OH, a cycloalkane, and a heterocycloalkane. In some embodiments, the cycloalkane and heterocycloalkane can be optionally substituted. Examples include, tiludronate acid, risedronate acid, and zoledronate acid. The chemical structures of exemplary bisphosphonic acids are shown below.

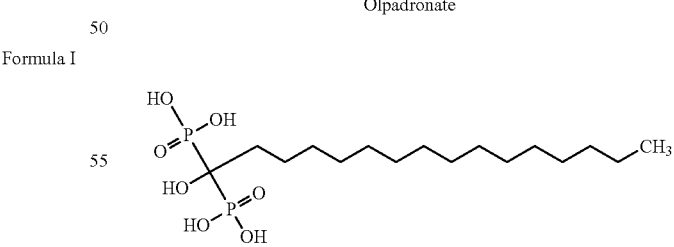

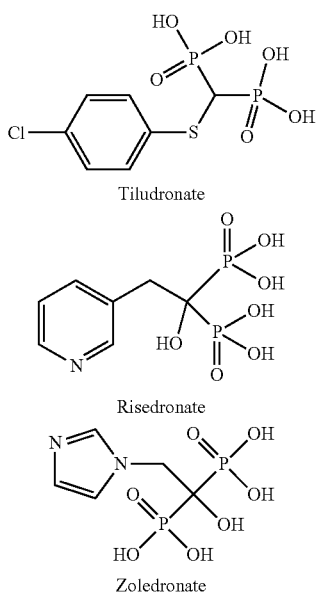

Tiludronate

Risedronate

Zoledronate

In some embodiments, triphosphonic acids can be used. For example, the polyphosphonic acid can be nitrilotri (methylphosphonic acid). The chemical structure of nitrilotri (methylphosphonic acid) is shown below.

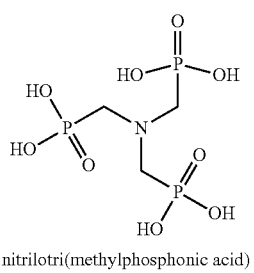 [SMILES: O=P(O)(O)CN(CP(=O)(O)O)CP(=O)(O)O]

nitrilotri(methylphosphonic acid)

Referring back to FIG. 1, the method of separating a sample comprising oligonucleotides and/or glycans also includes flow the sample and polyphosphonic acid through a liquid chromatography column (110) and separating the sample/oligonucleotides/glycans (115). The liquid chromatography column can be formed of metal. In some embodiments, the liquid chromatography column is formed of plastic, for example, PEEK.

When the sample includes oligonucleotides, the sample can include any oligonucleotide, for example, the sample can include antisense oligonucleotides (ASOs), small interfering RNAs (siRNA), small hairpin RNAs (shRNAs), and micro RNAs (miRNAs) as well as Aptamers and messenger RNAs (mRNAs). The sample can include oligonucleotides that range from about 20 to about 80 nucleotides, for example, the oligonucleotide can be about 20, 25, 30, 35, 40, 45, 50, 55, 60, 65, 70, 75, or 80 nucleotides long. In some embodiments, the oligonucleotide is an mRNA having a length of about 1,500 or more nucleotides long.

In some embodiments, the sample includes a phosphorylated oligonucleotide, e.g., an oligonucleotide that has been phosphorylated at one or both ends. In some embodiments, the oligonucleotide has a 5' phosphate or a 3' phosphate. The oligonucleotides present in the sample can include nucleotides where at least one nucleotide within the oligonucleotide is adenosine triphosphate (ATP). The structure of ATP is shown below.

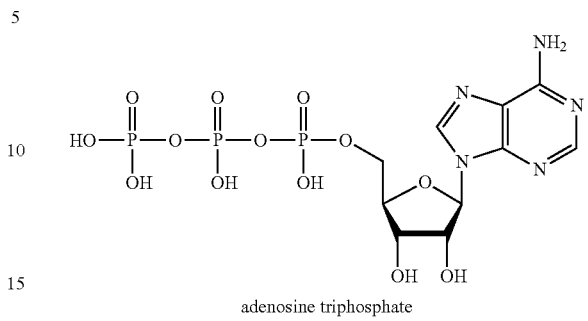

adenosine triphosphate

In some embodiments, the polyphosphonic acid is etidronic acid at a pH of 8.5 and the oligonucleotide include nucleotides where at least one nucleotide is ATP.

Referring to FIG. 2, in another aspect the technology features a method of performing solid phase extraction (200). The method 200 includes injecting a sample into a solid phase extraction (SPE) cartridge (205). The sample includes oligonucleotides, for example, any oligonucleotide described herein, and/or glycans. The SPE cartridge includes a stationary phase. The oligonucleotides and/or glycans are retained by the stationary phase. One of skill in the art will understand how to select a stationary phase material that will retain an oligonucleotide and/or glycan of interest.

The method 200 also includes washing the SPE cartridge with a polyphosphonic acid (210). The polyphosphonic acid is at a concentration of between about 0.01 M to about 1 M. The polyphosphonic acid elutes the oligonucleotides and/or glycans from the SPE cartridge.

As described above with respect to FIG. 1, a molar excess of polyphosphonic acid can be used. A molar excess is a concentration that is, for example, double or triple the concentration of the oligonucleotides or analytes in the sample. For example, the concentration of polyphosphonic acid can be between about 0.01 M to about 1 M. In some embodiments, the concentration of polyphosphonic acid is between about 0.01 M to about 0.1 M. In some embodiments, the concentration of polyphosphonic acid is between about 20 mM to about 50 mM or between about 30 mM to about 50 mM.

Alternatively, the concentration of polyphosphonic acid can be expressed in grams. In some embodiments, between about 1 pg to about 1 mg of polyphosphonic acid can be injected into the sample.

The polyphosphonic acid can be any of those as described with respect to FIG. 1 above, for example, etidronic acid or nitrilotri(methylphosphonic acid). As described above, the sample can include phosphorylated oligonucleotides, for example, oligonucleotides having nucleotides where at least one nucleotide is ATP.

In some embodiments, the walls of the SPE cartridge are formed of plastic, for example PEEK. The SPE cartridge can be a packed syringe or a well plate.

Kits

The technology can be provided in kits. For example, in some aspects the technology relates to kits for use in the separation of oligonucleotides and/or glycans using liquid chromatography. The kit can include a chromatography column packed with a stationary phase suitable to separate oligonucleotides and/or glycans. The kit can also include a vial comprising a polyphosphonic acid. The polyphosphonic acid can be any of those described herein. The kit can also include instructions for separating a sample comprising oligonucleotides and/or glycans. The instructions can be, for example, any one of the methods described herein.

In another aspect, the technology relates to kits for use in solid phase extraction of oligonucleotides and/or glycans. The kit can include a solid phase extraction cartridge packed with a stationary phase suitable to separate oligonucleotides and/or glycans. The kit can also include a vial comprising a polyphosphonic acid. The polyphosphonic acid can be any of those described herein. The kit can also include instructions for separating a sample comprising oligonucleotides and/or glycans. The instructions can be, for example, any one of the methods described herein.

In yet another aspect, the technology relates to kits for use in sample preparation of a biological material, such as, for example, but not limited to, oligonucleotides, glycans, or any phosphorylated compound. The kit can include glassware (e.g., sample vials, flasks, beakers, etc.) as well as a vial comprising a polyphosphonic acid. The polyphosphonic acid can be any of those described herein. The kit can also include instructions for sample preparation or preparing a calibration curve for the biological material.

In some embodiments, the solid phase extraction cartridge is a packed syringe. In some embodiments, the solid phase extraction cartridge is a well plate, for example, a 96-well plate.

EXAMPLES

Example 1: Recovery of GEM 91 Oligonucleotide from WAX SPE Plate

A sample comprising GEM 91, an antisense 25-mer oligonucleotide phosphorothioate, a therapeutic agent for AIDS, was separated using weak ion exchange (WAX) solid phase extraction (SPE). The SPE was performed using well plates following the protocol below:

Condition: 2×200 µL MeOH

Equilibrate: 3×200 µL of 50 mM NH$_4$Ac (pH 5.5)

Load: 200 µL GEM 91 oligonucleotide

Wash 1: 2×200 µL NH$_4$Ac (pH 5.5)

Wash 2: 1×200 µL 20% MeOH

Elute: 2×50 µL 50 mM TEA (triethylamine)/20% MeOH (pH 12.2)

Samples were analyzed using LC/MS employing the conditions detailed below. As shown in FIG. 3A, only 14% of the GEM 91 oligonucleotides was recovered. Recovery was calculated based upon a comparison to a sample of known concentration that was not passed through the SPE device.

The following conditions were used in this LC/MS analysis:

LC Conditions:

Mobile Phase A: 15 mM TEA, 400 mM HFIP (hexafluoro-2-propanol) pH 7.8

Mobile Phase B: 50% Mobile Phase A/50% Methanol pH 7.8

Injection volume: 10 µL

Column: Acquity BEH C18 1.7 µm, 2.1×50 mm

Temperature: 60° C.

| | Flow (mL/min) | % A | % B |
|---|---|---|---|
| initial | 0.5 | 75 | 25 |
| 1.0 | 0.5 | 75 | 25 |
| 2.0 | 0.5 | 5 | 95 |
| 3.0 | 0.5 | 5 | 95 |
| 3.5 | 0.5 | 75 | 25 |
| 4 | 0.5 | 75 | 25 |

MS Conditions:

| Name | Q1/Q3 | Cone | Collision |
|---|---|---|---|
| GEM 91 A | 863.1/95 | 60 | 58 |
| GEM 91 B | 971.0/95 | 60 | 68 |

Negative ESI Mode

Capillary Voltage—2 kV

Source Offset—50

Desolvation Temperature—400 C

Desolvation Gas—800 L/hr

Cone Gas—10 L/hr

Source Temp—120 C

The same SPE was performed again, but this time using etidronic acid to elute/wash the GEM 91 oligonucleotide from the well plate. FIG. 3B shows that 90% of the GEM 91 oligonucleotides was recovered when etidronic acid was used to elute/wash the oligonucleotides from the well plate.

A comparison of FIG. 3A to FIG. 3B shows that the MRM (multiple-reaction monitoring) chromatograms produced when etidronic acid is used have TIC (total ion current) signal count that is an order of magnitude better than when the SPE was done with MeOH and TEA (compare "MRM of 4 Channels ES—TIC 4.74e5" of FIG. 3B to "MRM of 4 Channels ES—TIC 2.24e4" of FIG. 3A).

Example 2: Generation of Calibration Curve for 25-Mer Oligonucleotide GEM 91

Figure 4B:
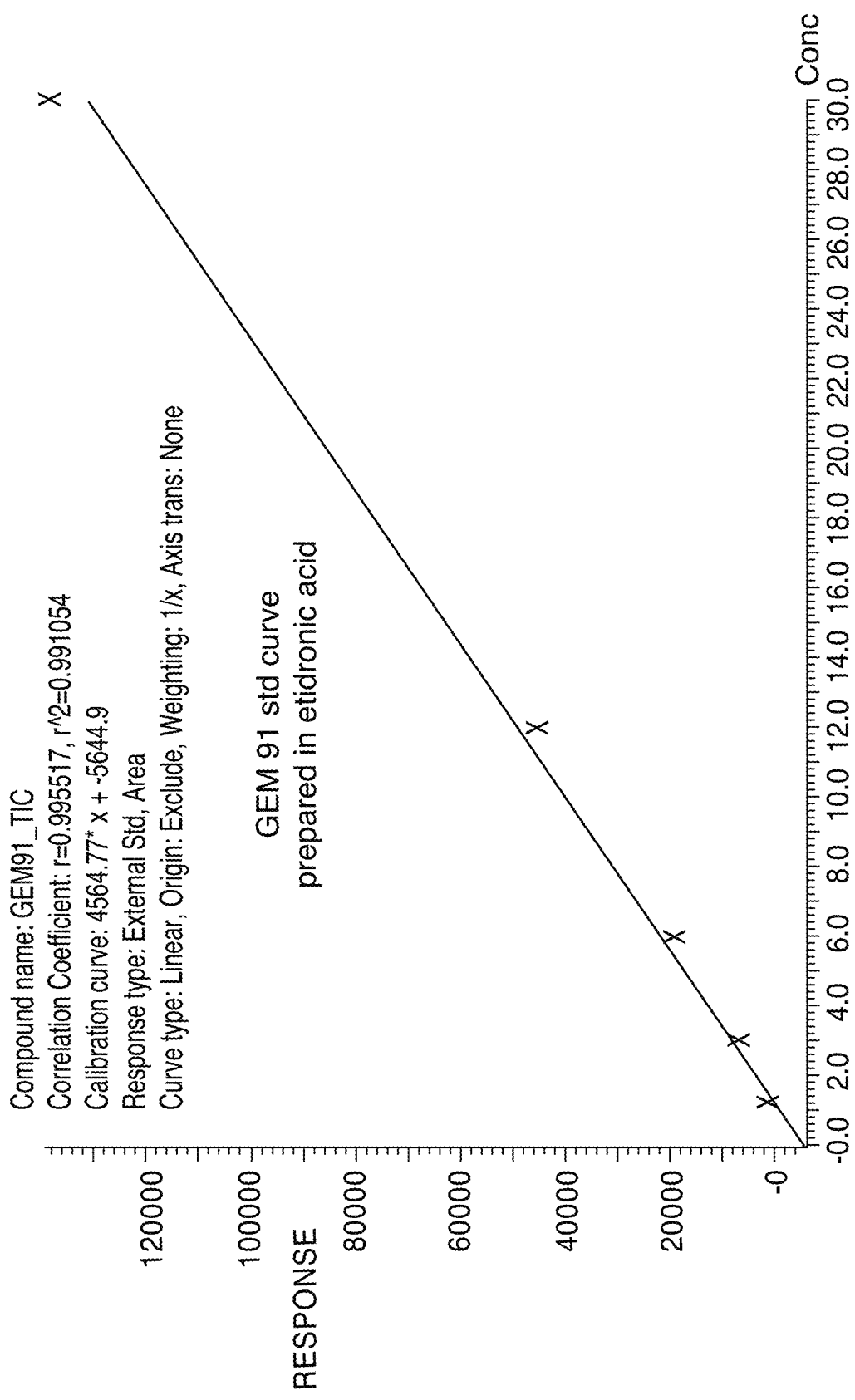
FIG. 4B is a linear calibration curve prepared for a 25-mer oligonucleotide GEM 91 prepared in etidronic acid, according to an illustrative embodiment of the technology.

Generation of a linear calibration curve is the most fundamental task in any quantitative bioanalytical study. Nonspecific binding of an analyte will render many of the lower concentration samples below the limit of detection and therefore dramatically impact results. In the example shown in FIGS. 4A and 4B, a standard curve is prepared for a 25-mer oligonucleotide GEM 91. Oligonucleotides are particularly prone to nonspecific binding. The samples of FIGS. 4A and 4B were prepared in glass sample vials. In the calibration curve in FIG. 4A, the standard being analyzed is an aqueous solution. It can be observed that the lower region of the curve is not detected because of the loss of signal due to the analyte being nonspecifically bound. When the same analyte is prepared in etidronic acid, FIG. 4B, the nonspecific binding of the analyte is eliminated, and the full linear dynamic range becomes useful data.

Example 3: Passivation of Stainless Steel Frits by Injection

Example 3 shows the passivation of stainless steel frits using different acids for the separation and detection of ATP (adenosine triphosphate). Injections were done every thirty seconds. The ATP and acid were injected onto a metal frit. The ATP sample used has a concentration of 55 ng/µL. A 0.2

μL injection injects 10 ng of ATP onto the stainless steel frit. The ATP sample is in 50% acetonitrile with 10 mM buffer pH 6.8 ammonium acetate.

Figure 5A:
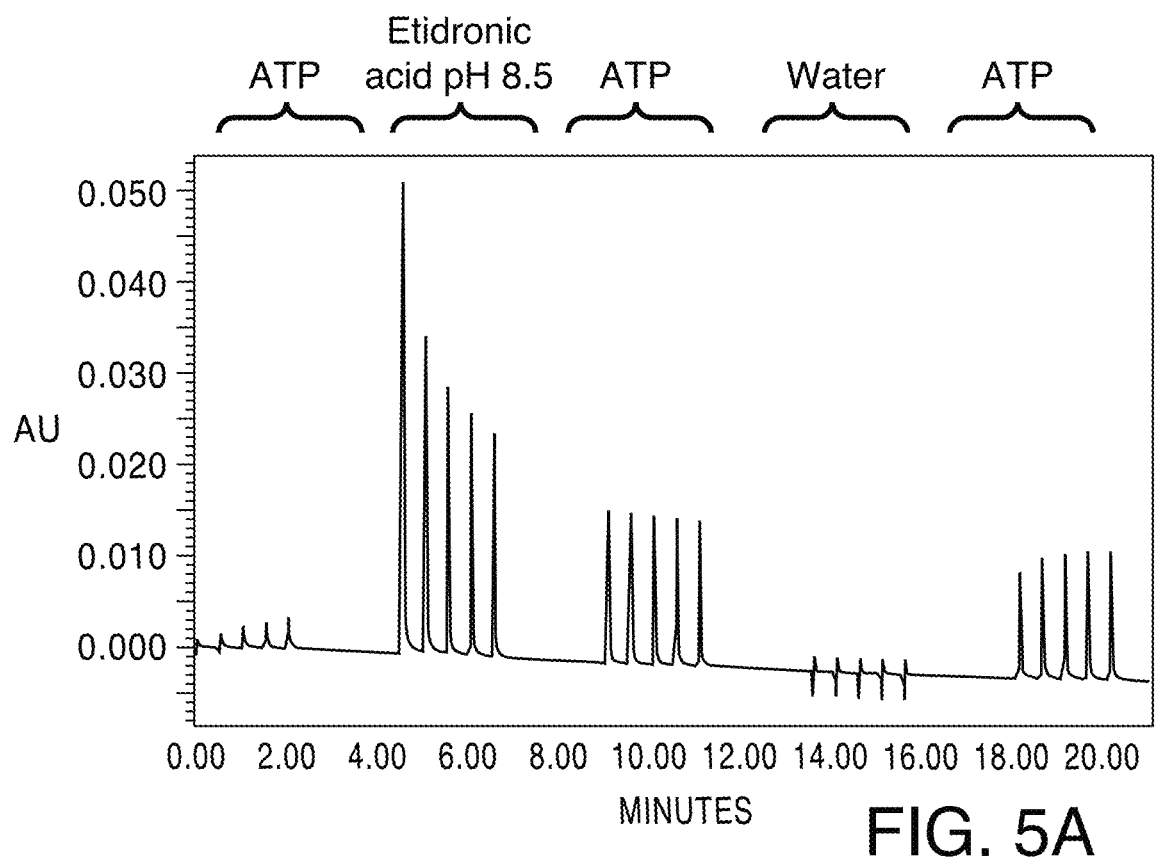
FIG. 5A is a chromatogram showing absorbance over time of a set of five 30 second injections of ATP on a stainless steel frit using etidronic acid to passivate the frit, according to an illustrative embodiment of the technology.

Referring to FIG. 5A, ATP is initially injected onto the stainless steel frit, five injections are made every 30 seconds. There is little to no signal due to the ATP interacting with the metal surface of the frit. However, there is a bit of a signal increase over the set of five injections. This is likely due to the ATP interacting with the metal surface of the frit, allowing later injections of ATP to elute without as much interference from the metallic surface, as at least a portion of the metallic surface has been passivated with prior ATP injections. However, since ATP is the analyte of interest, this is not an ideal situation.

Next, etidronic acid at a pH of 8.5 is injected onto the stainless steel frit, five injections every 30 seconds. Due to etidronic acid being fully charged (having two negative charges per phosphate), the etidronic acid has a good potential to be absorbed to the metal. The increased signal that is initially observed during the etidronic acid injections is the ATP eluting from the stainless steel frit as the etidronic acid displaces any ATP that has adhered to the metallic frit in the previous injection.

Still referring to FIG. 5A, after the injections of etidronic acid, ATP was again injected into the stainless steel frit, five injections every 30 seconds. The second set of ATP injections shows a much larger and more consistent signal than the first set. This indicates that the etidronic acid from the prior injection has adhered to the metallic surface of the frit and the ATP can elute without interference from the metal.

Water was then injected into the system and a third set of ATP injections, five injections every 30 seconds, was made. The third injection of ATP is still much larger than the first injection, but smaller than the second ATP injection. As can be seen from the third injection of ATP, the first injection in the five injection series is smaller and it gradually increases as each 30 second injection is made. This is likely due to the etidronic acid wearing off of the metallic frit. However, this second set of ATP injections after etidronic acid was used to passivate the frit, still provides good results and is much better than the initial set of ATP injections.

Figure 5B:
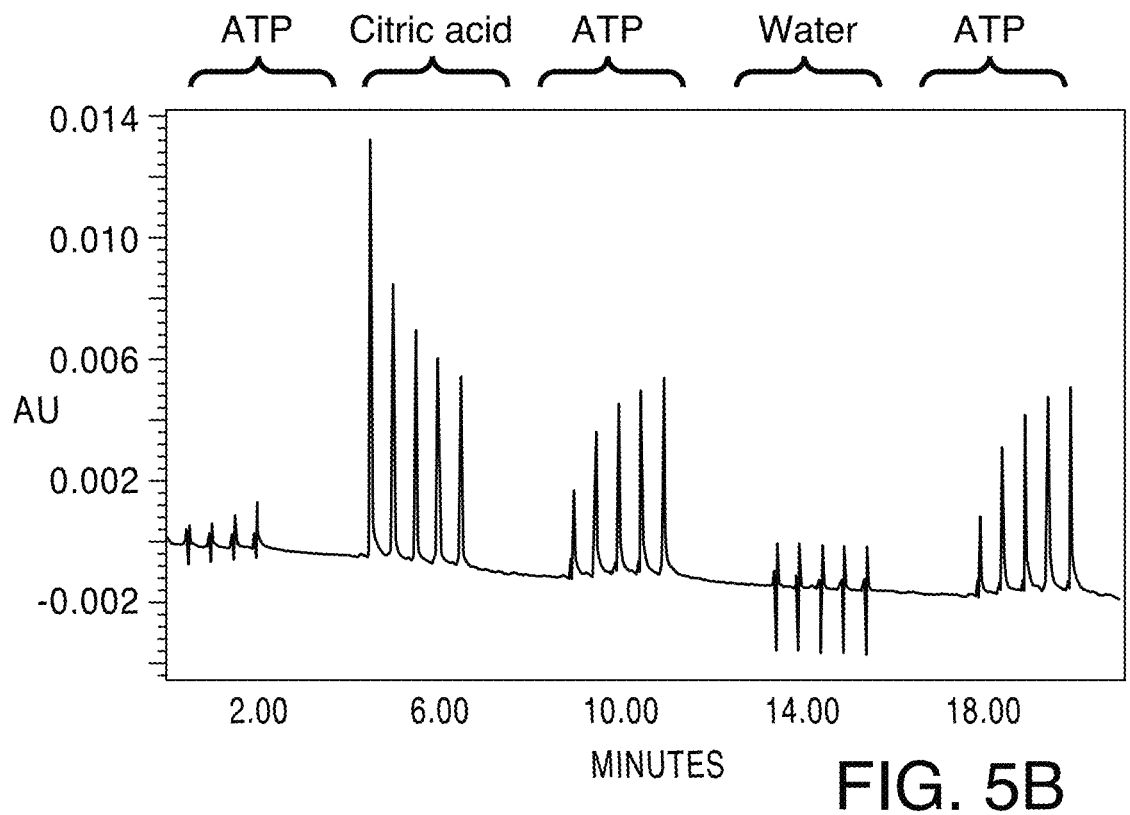
FIG. 5B is a chromatogram showing absorbance over time of a set of five 30 second injections of ATP on a stainless steel frit using citric acid to passivate the frit, according to an illustrative embodiment of the technology.

FIG. 5B is similar to FIG. 5A, except that citric acid is used instead of etidronic acid. As can be seen from a comparison of FIG. 5B to FIG. 5A, citric acid is not as good at passivating the metallic frit as etidronic acid. The second and third injections of ATP show increasing signal strength over the five injections, indicating that ATP is adhering to the metallic surface and not eluting through the frit. In other words, the citric acid did not passivate the metallic frit to the same extent that the etidronic acid passivated the metallic frit. Moreover, the signal strength of the ATP in FIG. 5A with the etidronic acid is about 0.015 AU while the signal strength of the ATP in FIG. 5B when citric acid is used in a degree of magnitude less, at about 0.006 AU.

Figure 5C:
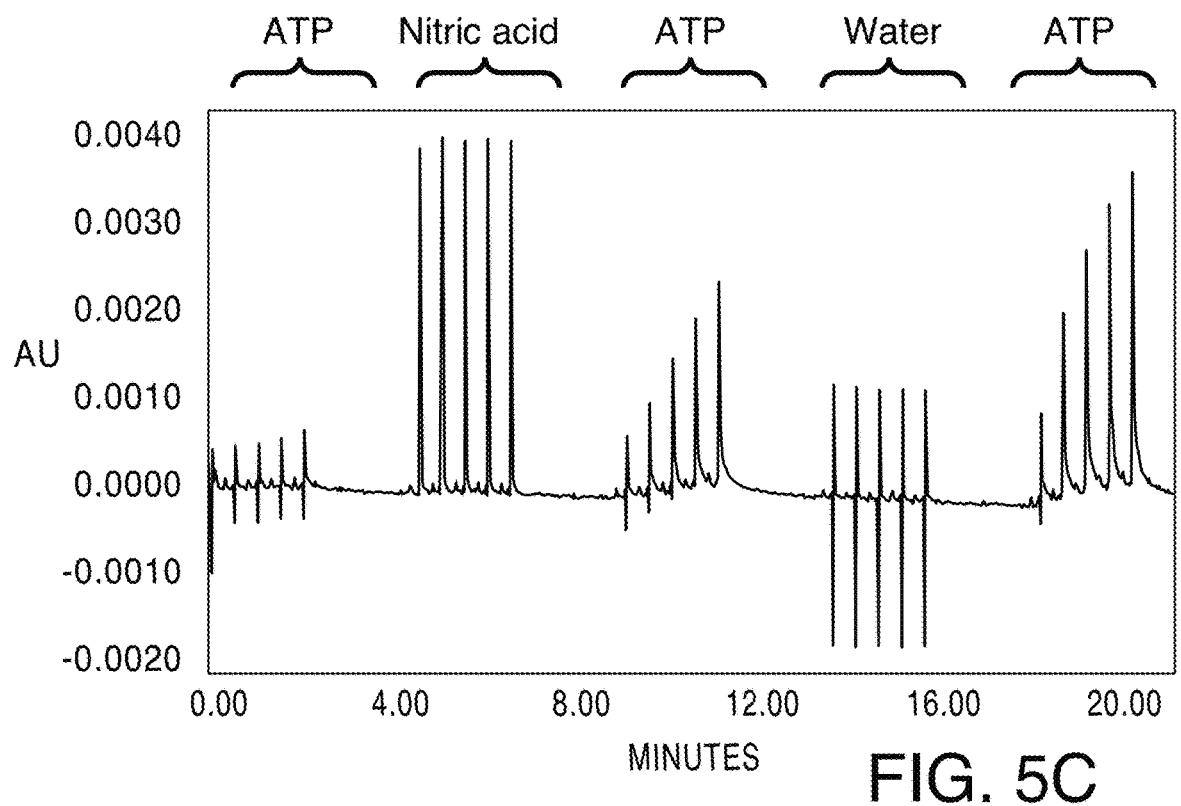
FIG. 5C is a chromatogram showing absorbance over time of a set of five 30 second injections of ATP on a stainless steel frit using nitric acid to passivate the frit, according to an illustrative embodiment of the technology.

FIG. 5C is similar to FIGS. 5A and 5B, except that nitric acid is used to passivate the metallic frit. As can be seen from a comparison of FIG. 5C to FIG. 5A, nitric acid is not as good at passivating the metallic frit as etidronic acid. The second and third injections of ATP show increasing signal strength over the five injections, indicating that ATP is adhering to the metallic surface and not eluting through the frit. In other words, the nitric acid did not passivate the metallic frit to the same extent that the etidronic acid passivated the metallic frit. Moreover, the signal strength of the ATP in FIG. 5A with the etidronic acid is about 0.015 AU while the signal strength of the ATP in FIG. 5C when nitric acid is used in a degree of magnitude less, at about between 0.0010 to about 0.0035 AU.

Figure 5D:
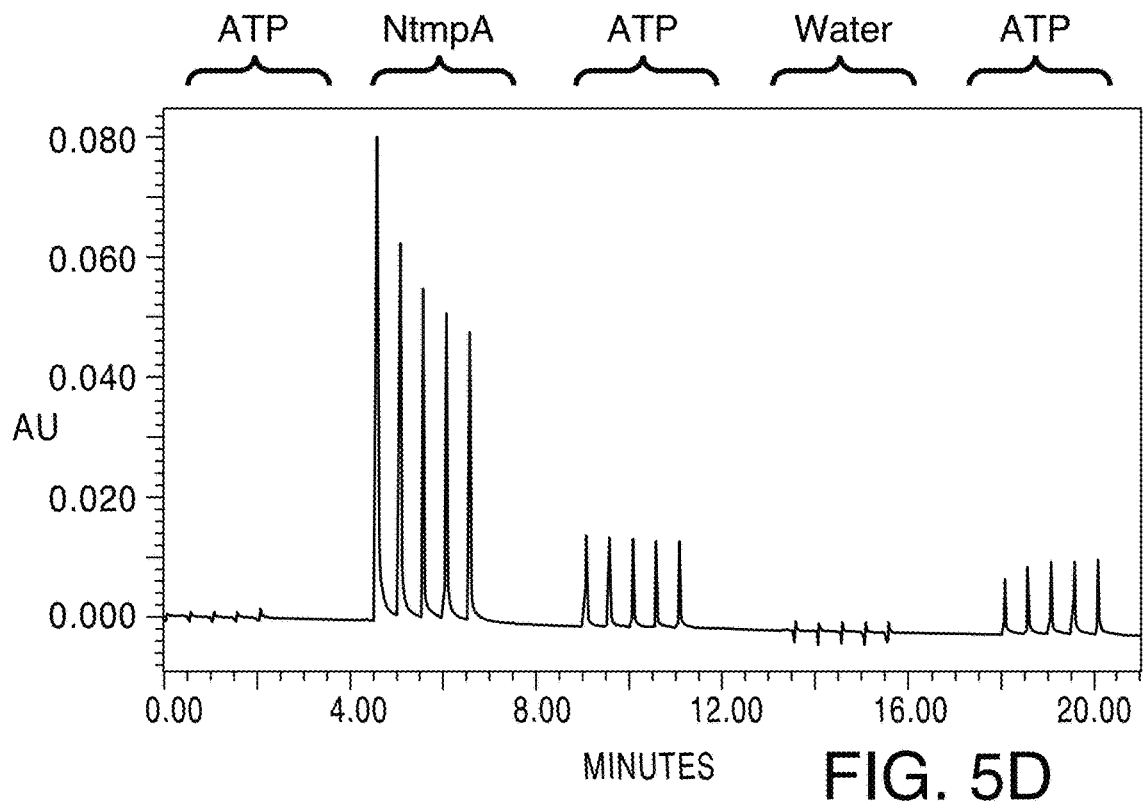
FIG. 5D is a chromatogram showing absorbance over time of a set of five 30 second injections of ATP on a stainless steel frit using nitrilotri(methylphosphoric acid) to passivate the frit, according to an illustrative embodiment of the technology.

FIG. 5D is similar to FIGS. 5A, 5B, and 5C except that nitrilotri(methylphosphoric acid) is used to passivate the metallic frit. As can be seen from a comparison of FIG. 5D to FIG. 5A, nitrilotri(methylphosphoric acid) is a good passivator. The second and third injections of ATP are relatively flat, each injection having an absorbance of about 0.015 AU. Similar to FIG. 4A, during the third set of injections of ATP, the first injection in the five injection series is smaller and it gradually increases as each 30 second injection is made. This is likely due to the nitrilotri(methylphosphoric acid) wearing off of the metallic frit. However, this second set of ATP injections after nitrilotri(methylphosphoric acid) was used to passivate the frit, still provides good results and is much better than the initial set of ATP injections.

Example 4: Longevity Following a Single Injection

Figure 6A:
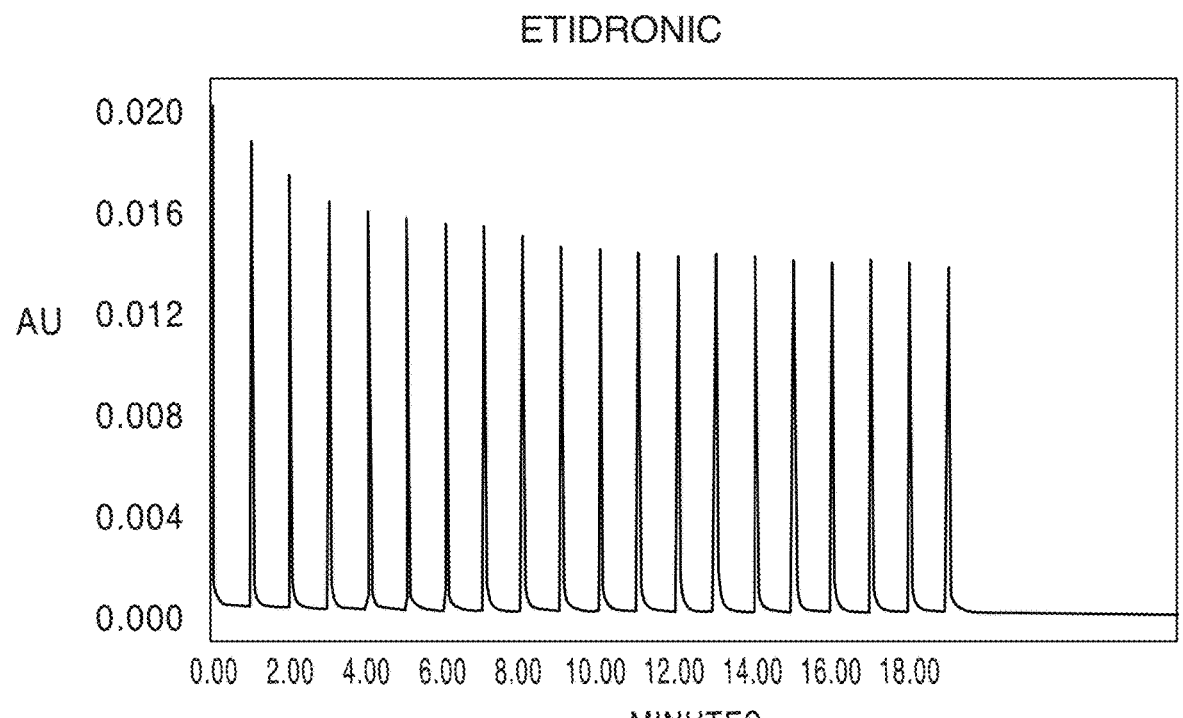
FIG. 6A is a chromatogram showing the longevity of a single injection of etidronic acid followed by 20 injections of ATP spaced one minute apart, according to an illustrative embodiment of the technology.
Figure 6B:
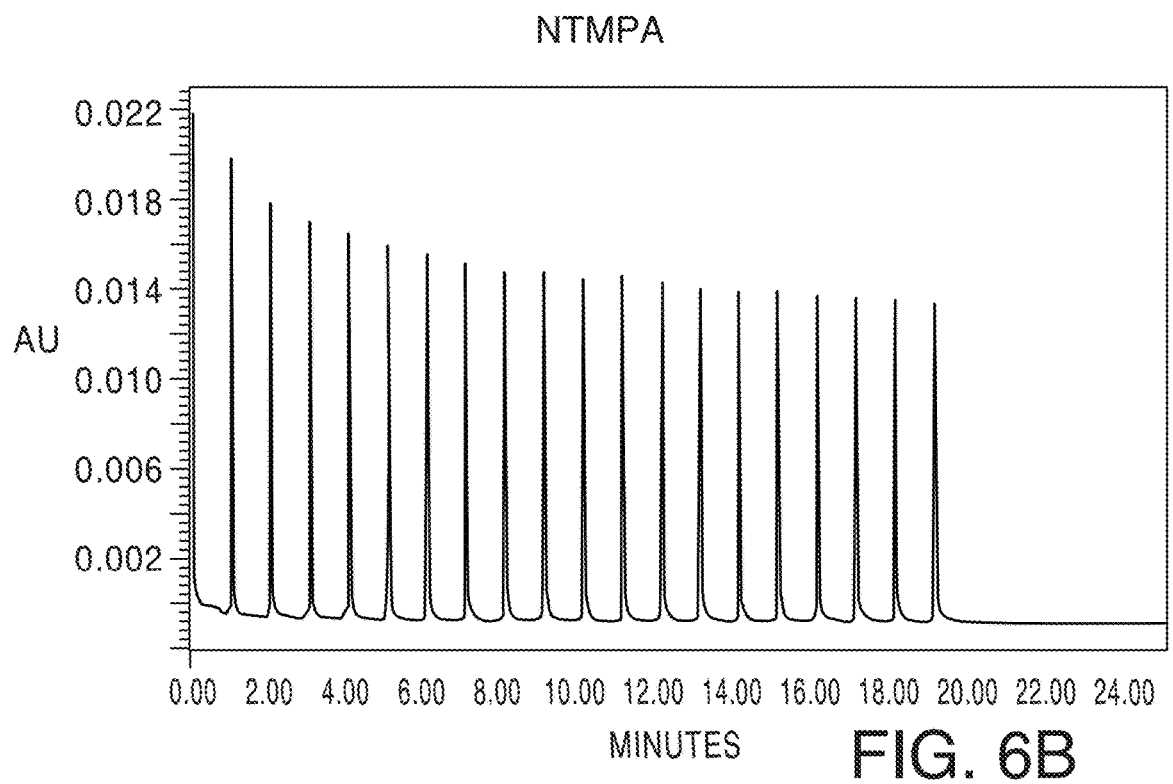
FIG. 6B is a chromatogram showing the longevity of a single injection of nitrilotri(methylphosphoric acid) followed by 20 injections of ATP spaced one minute apart, according to an illustrative embodiment of the technology.

Example 4 relates to how long a single 2 μL injection of etidronic acid or nitrilotri(methylphosphoric acid) (NTMPA) passivation lasts. FIGS. 6A and 6B show a two μL injection of etidronic acid (FIG. 6A) and NTMPA (FIG. 6B) followed by 20 ATP injections (0.2 μL per injection) spaced one minute apart. Similar to Example 2, a stainless steel frit was used for Example 3.

FIGS. 6A and 6B show that the passivation provided by etidronic acid or nitrilotri(methylphosphoric acid) is temporary. As can be seen from FIGS. 6A and 6B, the absorbance of ATP slowly decreases with each injection of ATP. This shows that the effects of the passivation slowly wear off.

Example 5: High Recovery, High Sensitivity of Phosphoglycan Analysis

Anionic glycans can be difficult to analyze by liquid chromatography because of their propensity to adsorb to metal surfaces. While multiply sialylated analytes can be difficult to recover, this challenge is most obvious with phosphorylated glycans. Nevertheless, it is critical to have accurate assays for the characterization and quantitation of phosphorylated glycans, given that they can be found as post-translational modifications on proteins of therapeutic value and can be of direct impact to cellular uptake. Enzyme replacement therapies for lysosomal storage disorders are a defining example of a therapeutic class wherein phosphorylated glycans frequently represent a critical quality attribute. With the instant technology, it has been discovered that polyphosphonic acids, including but not limited to etidronic acid, can be added to samples to dramatically improve the recovery of phosphorylated glycans during an LC-based analysis. As shown in this example, a standard N-glycan sample preparation technique leads to the detection of little to no phosphorylated glycan. If etidronic acid is instead added to the sample prior to its injection onto an LC-MS system, 10 to 1000× increases in sample recovery and sensitivity can be achieved.

N-Glycans were prepared from recombinant glucuronidase using a GlycoWorks RapiFluor-MS N-Glycan kits according to manufacturer recommendations. Aqueous samples were prepared to the point of being derivatized with RapiFluor-MS and 4 μL of 500 mM etidronic Acid (neutralized with ammonium hydroxide) was added to a 40 μL volume of the reaction mixture. Solid phase extraction was not employed and a 1 μL volume of aqueous sample was injected onto a 2.1×50 mm ACQUITY® UPLC® Glycan BEH Amide 1.7 µm 130 Å column (commercially available from Waters Technologies Corporation, Milford, MA) heated to a temperature of 60° C. An LC-fluorescence-MS analysis was thereby performed using an ACQUITY® UPLC® H-Class Bio outfitted with a fluorescence detector and XEVO® G2-XS QTof mass spectrometer (commercially available from Waters Technologies Corporation, Milford, MA). To ensure that the non-volatile components of the sample were not eluted into the mass spectrometer, chromatographic effluent was diverted to waste for the first 3 minutes of the run. Selective detection of a mannose 7 glycan containing two man-6-phosphate residues was achieved through a visualization of extracted ion chromatograms (1015.84±0.2 m/z). Gradient and flow rate conditions were as follows:

| Time (min) | Flow Rate (mL/min) | % C 50 mM ammonium formate (pH 4.4) | % D acetonitrile | Curve |
| --- | --- | --- | --- | --- |
| Initial | 0.400 | 25.0 | 75.0 | Initial |
| 11.66 | 0.400 | 46.0 | 54.0 | 6 |
| 12.16 | 0.200 | 100.0 | 0.0 | 6 |
| 13.16 | 0.200 | 100.0 | 0.0 | 6 |
| 14.36 | 0.200 | 25.0 | 75.0 | 6 |
| 15.86 | 0.400 | 25.0 | 75.0 | 6 |
| 18.33 | 0.400 | 25.0 | 75.0 | 6 |

Figure 7A:
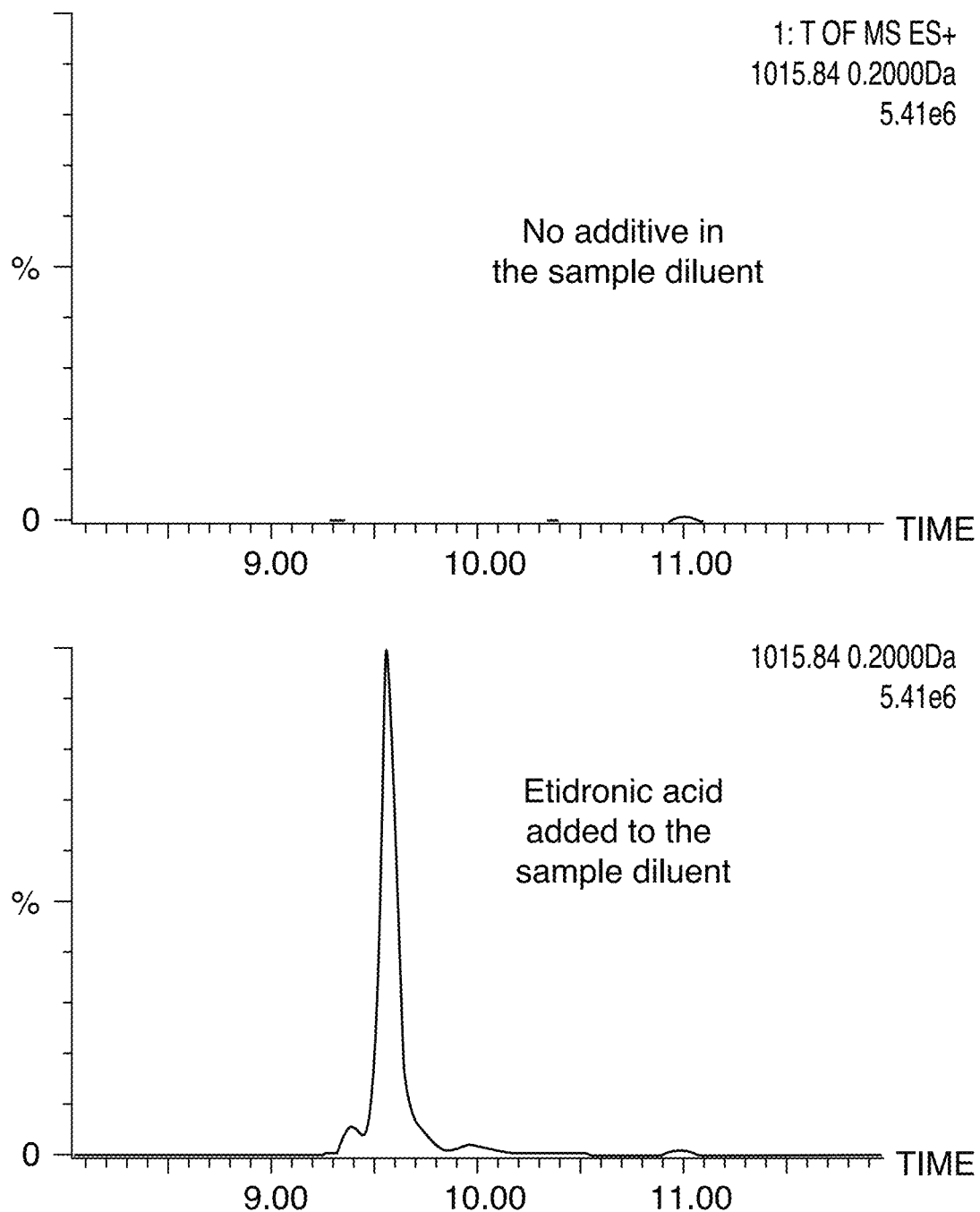
FIG. 7A are extracted ion chromatograms for Man-7 with two Man-6-Phosphate residues (Man7-PP; 1015.84±0.2 m/z) as obtained from a sample containing (bottom) and not containing etidronic acid (top), according to an illustrative embodiment of the technology.
Figure 7B:
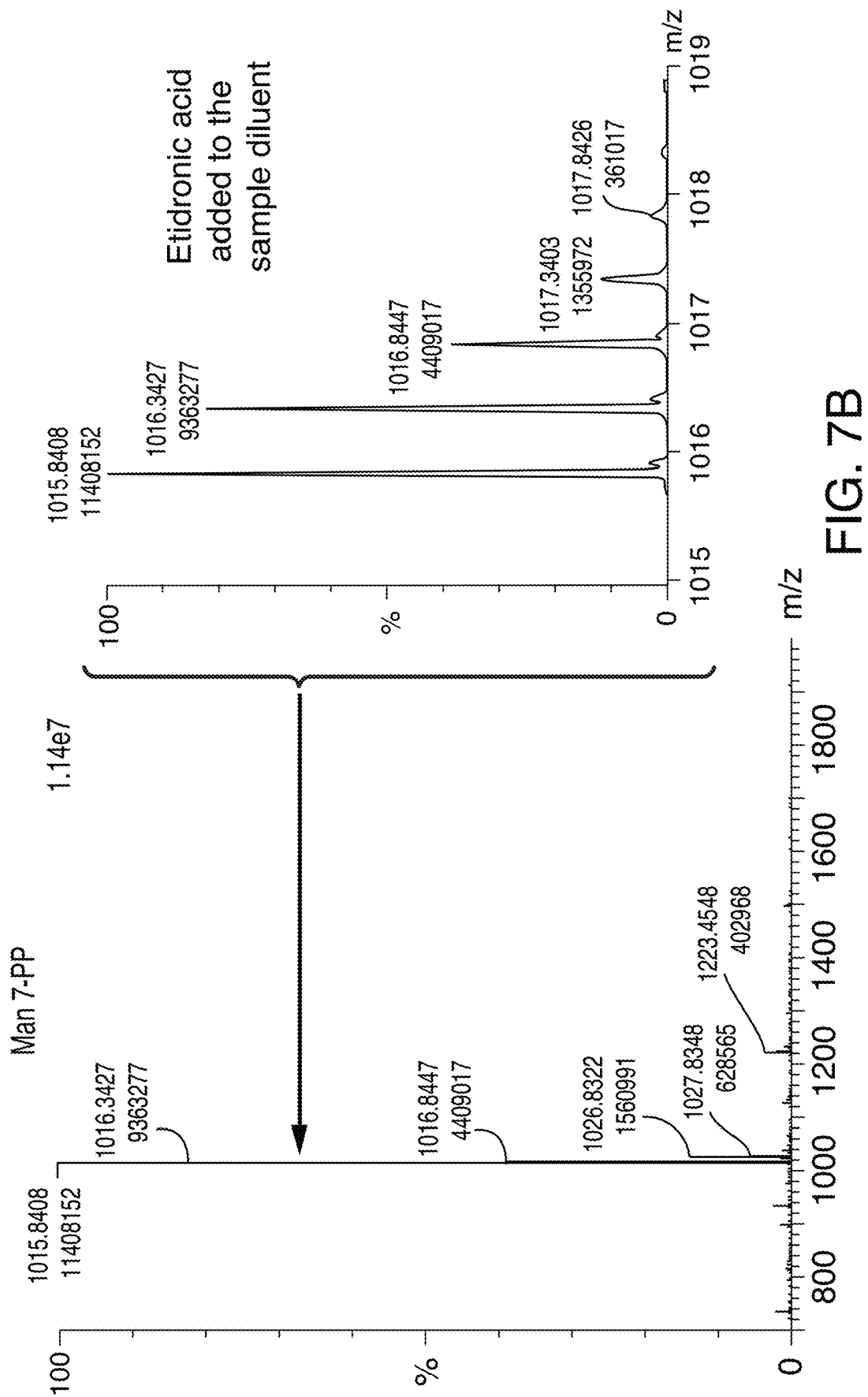
FIG. 7B is a mass spectrum of a Man-7 glycan containing two Man-6-Phosphate residues as obtained from an etidronic containing sample diluent, according to an illustrative embodiment of the technology.

FIGS. 7A and 7B show LC-MS analysis of phosphorylated Man-7 Glycan as facilitated with sample diluent containing etidronic acid. FIG. 7A are extracted ion chromatograms for Man-7 with two Man-6-Phosphate residues (Man7-PP; 1015.84±0.2 m/z) as obtained from a sample containing (bottom) and not containing etidronic acid (top). FIG. 7B is a mass spectrum of a Man-7 glycan containing two Man-6-Phosphate residues as obtained from an etidronic containing sample diluent.

Figure 8A:
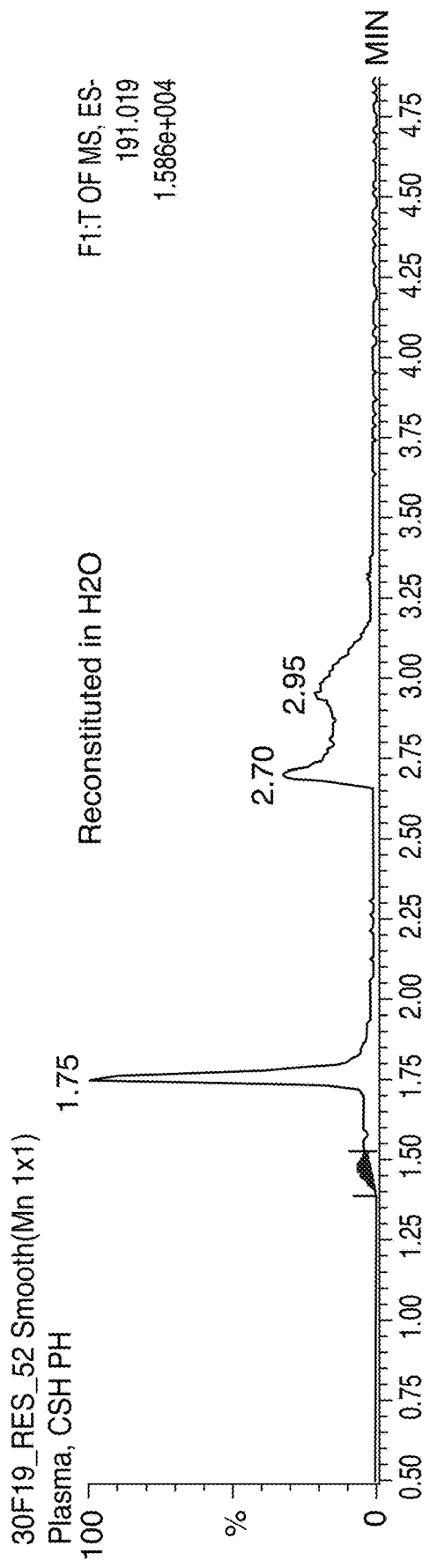
FIG. 8A is a chromatogram showing the effect of etidronic acid addition to eliminate nonspecific binding with isocitric acid, where the sample of isocitric acid is reconstituted in water, according to an illustrative embodiment of the technology.
Figure 8B:
FIG. 8B is a chromatogram showing the effect of etidronic acid addition to eliminate nonspecific binding with isocitric acid, where the sample of isocitric acid is reconstituted in water and 0.1 mM etidronic acid, according to an illustrative embodiment of the technology.
Figure 8C:
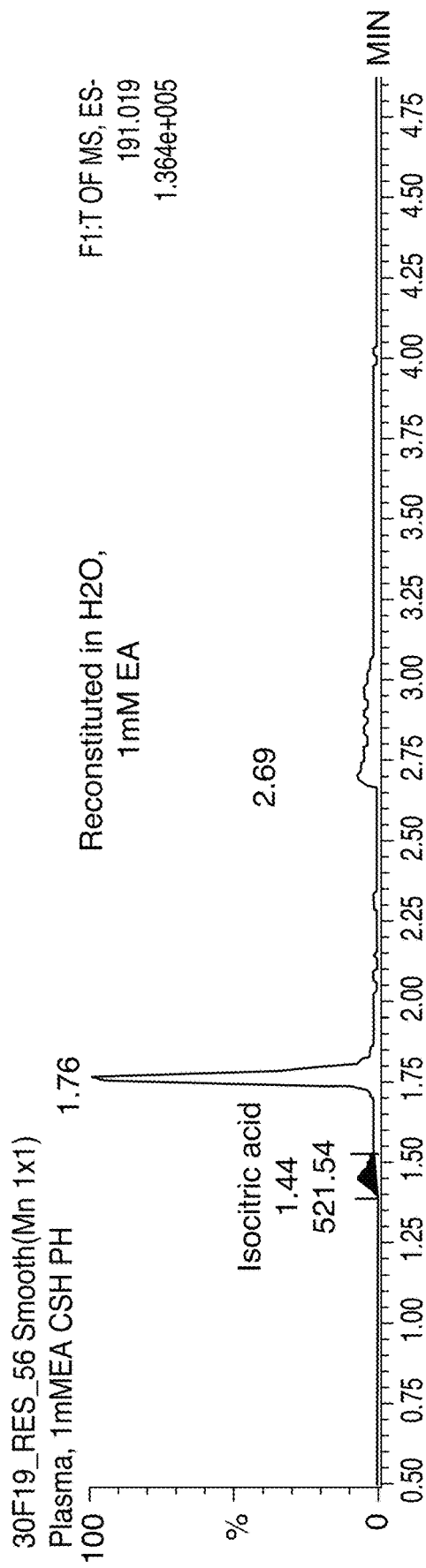
FIG. 8C is a chromatogram showing the effect of etidronic acid addition to eliminate nonspecific binding with isocitric acid, where the sample of isocitric acid is reconstituted in water and 1 mM etidronic acid, according to an illustrative embodiment of the technology.
Figure 8D:
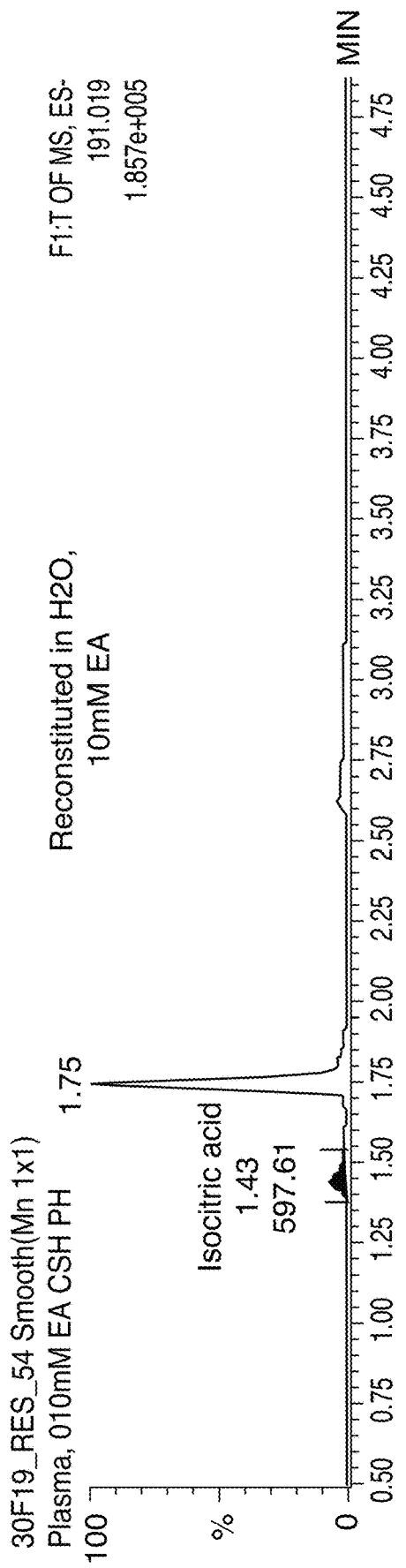
FIG. 8D is a chromatogram showing the effect of etidronic acid addition to eliminate nonspecific binding with isocitric acid, where the sample of isocitric acid is reconstituted in water and 10 mM etidronic acid, according to an illustrative embodiment of the technology.
Figure 8E:
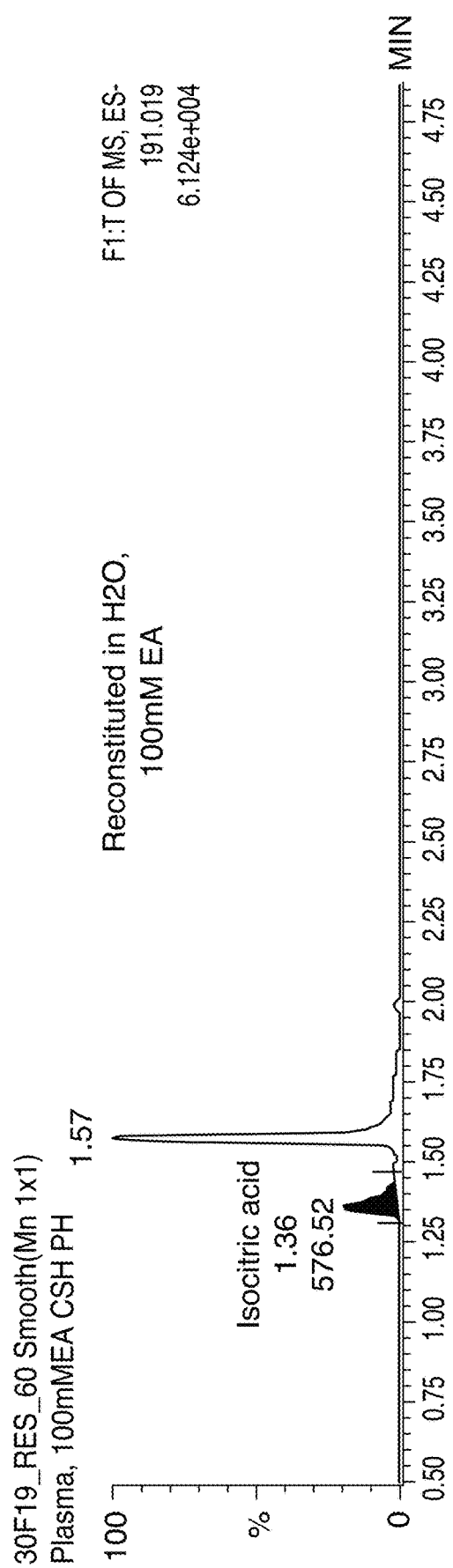
FIG. 8E is a chromatogram showing the effect of etidronic acid addition to eliminate nonspecific binding with isocitric acid, where the sample of isocitric acid is reconstituted in water and 100 mM etidronic acid, according to an illustrative embodiment of the technology.

Example 6: Effect of Etidronic Acid Eliminates Nonspecific Binding with Isocitric Acid Analyte The effect of etidronic acid addition to eliminate nonspecific binding is further demonstrated with the example of LC/MS analysis of isocitric acid. Referring to FIG. 8A, a small area is highlighted at 1.50 minutes where the isocitric acid should elute. A much larger area appears at 2.7 minutes as a large blob. That larger area is the isocitric acid being retained on metallic systems components such as column body and frits, and slowly eluted off as the gradient changes. As the concentration of etidronic acid increases from 0.1 mM to 100 mM (see FIGS. 8B-8E), we can observe that the nonspecific binding of isocitric acid on the systems starts to decrease (as evidenced by the loss of signal at 2.69 minutes) and a well-defined peak for isocitric acid appears at the expected retention time.

The following conditions were used in this LC/MS analysis:
LC Conditions:
Mobile Phase A: 0.1% formic acid in water
Mobile Phase B: 0.1% formic acid in acetonitrile
Injection volume: 3 µL
Column: ACQUITY UPLC® CSH Phenyl Hexyl 1.7 µm, 2.1×100 mm
Temperature: 50° C.

| | Flow (mL/min) | % A | % B |
| --- | --- | --- | --- |
| initial | 0.4 | 98 | 2 |
| 0.5 | 0.4 | 98 | 2 |
| 3.0 | 0.4 | 75 | 25 |
| 3.1 | 0.4 | 5 | 95 |
| 4.1 | 0.4 | 5 | 95 |
| 4.2 | 0.4 | 98 | 2 |

MS Conditions:
Negative ESI Mode, 40-950 m/z
Capillary Voltage—2 kV
Source Offset—50
Desolvation Temperature—400 C
Desolvation Gas—800 L/hr
Cone Gas—10 L/hr
Source Temp—120 C Example 7: Effect of a Titanium Frit Deactivated with an Inert Coating of Hybrid Organic-Inorganic Silica on Non-Specific Adsorption of 25-Mer Phosphorothioate Oligonucleotide (GEM 91)

Example 7 compares non-specific adsorption of a sample for a titanium frit deactivated with an inert coating of hybrid organic-inorganic silica (FIG. 9A) versus a stainless steel frit (FIG. 9B). The sample was a 25-mer phosphorothioate oligonucleotide and investigated with the following experimental conditions of a mobile phase of 5 mM ammonium acetate with pH 6, a flow rate of 0.2 mL/min, repetitive injection each 0.5 minutes apart, and only a 4.6 mm inner diameter HPLC frit in the sample flow path (no column in this experiment). The injected sample was detected by UV at 260 nm. Three different concentration levels of the sample were injected. In the first 10 injections, 31.1 ng of oligonucleotide was injected, followed by 10 injections of 62.2 ng of oligonucleotide, and followed by 10 injections of 155.5 ng oligonucleotide.

FIG. 9A is a chromatogram showing absorbance over time of three different concentration levels of 25-mer phosphorothioate oligonucleotide, including a titanium frit deactivated with an inert coating of hybrid organic-inorganic silica, according to an illustrative embodiment of the technology. No non-specific adsorption of 25-mer phosphorothioate oligonucleotide was apparent (no signal loss).

FIG. 9B is a chromatogram showing absorbance over time of three different concentration levels of 25-mer phosphorothioate oligonucleotide, including a stainless steel frit, according to an illustrative embodiment of the technology. In contrast to the titanium frit of FIG. 9A, non-specific adsorption was apparent (signal loss) for the stainless steel frit. The first ten, low level injections were completely lost, adsorbed on metal surface. Upon multiple injections, the signal improved due to the saturation of the stainless steel surface with and excess of the sample.

Below is nucleotide sequence for Trecovirsen (GEM91), 25-mer phosphorothioate oligonucleotide:

```
CTC TCG CAC CCA TCT CTC TCC TTC T
```

Example 8: Effect of Passivation of Stainless Steel Frits with Various Acids

Example 8 displays a series of experiments, that investigated the passivation of stainless steel frits with various acids including etidronic acid. The stainless steel frits were sonicated for 15 minutes at 50° C. in the solution indicated in FIGS. 10A-10I. The sample was a 25-mer phosphorothioate oligonucleotide and investigated with the following experimental conditions of a mobile phase of 5 mM ammonium acetate with pH 6, a flow rate of 0.2 mL/min, repetitive injection each 0.5 minutes, and only a 4.6 mm inner diameter HPLC frit was in the sample flow path (no column in this experiment). The injected sample was detected by UV at 260 nm.

FIGS. 10A-10I are chromatograms showing absorbance over time of three different concentration levels of 25 mer phosphorothioate oligonucleotide injected on a sonicated stainless steel frit with phosphoric acid (75 mM $H_3PO_4$) (FIG. 10A) and its buffer (75 mM $(NH_4)_2HPO_4$) titrated to pH 5.7 (FIG. 10B), 10% citric acid (FIG. 10C) and its buffer (10% $(NH_4)_3$ citrate) titrated to pH 7 (FIG. 10D), 0.6M etidronic acid (FIG. 10E) and its buffer (0.6M etidronate $NH_4$) titrated to pH 7 (FIG. 10F), 10% formic acid (FIG. 10G), 1 mM ethylenediaminetetraacetic acid (EDTA) (FIG. 10H), and 10% nitric acid (FIG. 10I), according to an illustrative embodiment of the technology.

Without wishing to be bound by theory, frit surface passivation is believed either due to excess of the sample that saturates the active adsorption sites or due to adsorption of competitive agents, such as multivalent acids anions (e.g., phosphate, citrate, or etidronate). These ions can be used directly as acids or as buffered solutions—salts (FIGS. 10A-10F). Phosphoric, citric and etidronic acids (including their buffers titrated to pH 5.7-7) are capable of conditioning the frit surface (FIGS. 10A-10F). No significant loss of oligonucleotide signal was observed with the conditioned frits.

No conditioning effect were observed for formic, nitric and EDTA acids (FIG. 10G, FIG. 10H, and FIG. 10I). Formic acid or nitric acid did not have any positive effect on sample recovery—they offered no protection (FIG. 10G and FIG. 10H). EDTA acid did not condition the stainless steel frit surfaces (FIG. 10I).

In after washing the passivated frits with "a diluted ammonium hydroxide to wash the frits after conditioning with phosphate/citrate/etidronate and saw partial loss of conditioning." The longevity of the conditioning appeared to be about 100 minutes.

Below is the chemical structure of 1,1-bis(phosphonic acid) (etidronic acid).

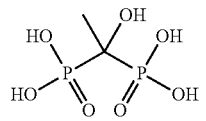

1,1-bis(phosphonic acid) (etidronic acid)

Example 9: Effect of Stainless Steel Frit Conditioning on Sample Recovery

Example 9 compares stainless steel frit conditioning via sample recovery of adenosine 5'-α,β-methylene) diphosphate (AMPcP), which is sensitive to metal surface adsorption (similar to oligonucleotides). The experimental conditions included a mobile phase of 5 mM ammonium acetate with pH 6, a flow rate of 0.2 mL/minute, and only a 4.6 mm inner diameter HPLC frit in the sample flow path (no column). The experiment was performed by injecting 50 ng of AMPcP in 9 or 10 injection series spaced by 10-minute gaps.

FIG. 11A is a chromatogram showing injections of adenosine 5'-α,β-methylene) diphosphate (AMPcP) with experimental conditions including a stainless steel frit that was first conditioned with five series of 10 μL injections (5×10 μL injections) of 0.6M $NH_4$ etidronate pH 7 solution, which was injected via a liquid chromatography autosampler, according to an illustrative embodiment of the technology.

After the frit conditioning, the AMPcP sample was injected via nine series of 10 injections (9×10 injections). Based on the experimental results as shown in FIG. 11A, it can be seen that the frit conditioning with 0.6M $NH_4$ etidronate pH 7 solution is temporary. The recovery was initially good (95%). However, the recovery began to decrease and the peaks began tailing.

FIG. 11B is a chromatogram showing injections of adenosine 5'-α,β-methylene) diphosphate (AMPcP) with including a conditioned stainless steel frit sonicated in 1% phosphoric acid for 15 minutes, according to an illustrative embodiment of the technology.

After the frit conditioning, the AMPcP sample was injected via ten series of 10 injections (10×10 injections). In contrast to the conditioning of the FIG. 11A example, the conditioning of the FIG. 11B example appears to be more stable. No loss of recovery was observed during the experiment of FIG. 11B.

Below is the chemical structure of adenosine 5'-α,β-methylene) diphosphate (AMPcP).

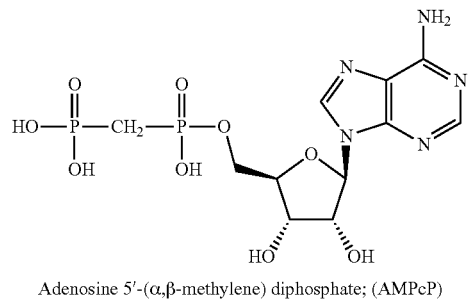 [SMILES: Nc1ncnc2c1ncn2[C@@H]1O[C@H](COP(=O)(O)CP(=O)(O)O)[C@@H](O)[C@H]1O]

Adenosine 5'-(α,β-methylene) diphosphate; (AMPcP)

Additional Embodiments

While a number of examples have been described, the present disclosure is not to be so limited. The present disclosure includes additional non-limiting examples. For example, without wishing to be bound by theory, after washing the passivated frits with a diluted ammonium hydroxide to wash the frits after conditioning with phosphate/citrate/etidronate, the frits may experience a partial loss of conditioning. The longevity of the conditioning could be affected, such as a partial loss of conditioning experiences after about 100 minutes.

What is claimed is:

1. A method of performing solid phase extraction comprising:
injecting a sample comprising oligonucleotides into a solid phase extraction cartridge comprising a stationary phase, wherein the oligonucleotides are retained by the stationary phase;
washing the solid phase extraction cartridge with a polyphosphonic acid at a concentration of between about 0.01 M to about 1 M to elute the oligonucleotides from the solid phase extraction cartridge.

2. The method of claim 1, wherein the concentration of polyphosphonic acid is between about 0.01 M to about 0.1 M.

3. The method of claim 2, wherein the concentration of polyphosphonic acid is between about 20 mM to about 50 mM.

4. The method of claim 3, wherein the concentration of polyphosphonic acid is between about 30 mM to about 40 mM.

5. The method of claim 1, wherein between about 1 pg to about 1 mg of the polyphosphonic acid is injected into the sample.

6. The method of claim 1, wherein the polyphosphonic acid is etidronic acid.

7. The method of claim 1, wherein the polyphosphonic acid is nitrilotri(methylphosphonic acid).

8. The method of claim 1, wherein walls of the solid phase extraction cartridge are formed of plastic.

9. The method of claim 1, wherein the sample comprises phosphorylated oligonucleotides.

10. The method of claim 9, wherein the phosphorylated oligonucleotides comprise nucleotides and at least one nucleotide is adenosine triphosphate.

11. The method of claim 1, wherein the polyphosphonic acid is etidronic acid at pH of 8.5 and the oligonucleotide comprises nucleotides and at least one nucleotide is adenosine triphosphate.

12. The method of claim 1, wherein the polyphosphonic acid is a bisphosphonic acid.

13. The method of claim 12, wherein the bisphosphonic acid is selected from the group consisting of clodronic acid, pamidronic acid, alendronic acid, neridronic acid, and olpadronic acid.

14. The method of claim 1, wherein the solid phase extraction cartridge is a packed syringe.

15. The method of claim 1, wherein the solid phase extraction cartridge is a well plate.

* * * * *